US005561042A

United States Patent [19]

Weis et al.

[11] Patent Number: 5,561,042
[45] Date of Patent: Oct. 1, 1996

[54] DIAMINE PLATINUM NAPHTHALIMIDE COMPLEXES AS ANTITUMOR AGENTS

[75] Inventors: Alexander L. Weis; Shih-Fong Chen; Peech S. Reddy; Mallaiah Mittakanti, all of San Antonio, Tex.; Daniel L. Dexter, Holcombe, Wis.; Jan M. Woynarowski, San Antonio, Tex.

[73] Assignee: Cancer Therapy and Research Center, San Antonio, Tex.

[21] Appl. No.: 380,841

[22] Filed: Jan. 30, 1995

Related U.S. Application Data

[63] Continuation-in-part of Ser. No. 279,173, Jul. 22, 1994.
[51] Int. Cl.$^6$ .............................. C12Q 1/68; C07F 15/00
[52] U.S. Cl. ........................... 435/6; 514/296; 546/98; 556/136
[58] Field of Search .......................... 435/6; 514/296; 546/98, 99, 100; 556/136

[56] References Cited

U.S. PATENT DOCUMENTS

| | | | |
|---|---|---|---|
| 4,841,052 | 6/1989 | Harnisch et al. | 544/361 |
| 4,874,863 | 10/1989 | Brana et al. | 540/99 |
| 5,086,059 | 2/1992 | Ardecky et al. | 514/284 |
| 5,206,249 | 4/1993 | Sun | 514/296 |
| 5,206,250 | 4/1993 | Sun | 514/296 |
| 5,235,045 | 8/1993 | Lewis et al. | 534/560 |
| 5,376,664 | 12/1994 | Kaltenbach | 514/296 |

FOREIGN PATENT DOCUMENTS

| | | |
|---|---|---|
| 0037486 | 3/1981 | European Pat. Off. . |
| 0281902 | 8/1988 | European Pat. Off. . |
| 0462800 | 6/1991 | European Pat. Off. . |
| 0481802 | 10/1991 | European Pat. Off. . |
| WO92/17454 | 10/1992 | WIPO . |
| WO92/17454 | 10/1992 | WIPO . |
| WO94/02466 | 2/1994 | WIPO . |

OTHER PUBLICATIONS

Clark G., Anti-Cancer Compounds . . . Acta Crystallographica C45 Part 1 (1989) pp. 67–71.
Kirshenbaum M., (R,R)-2,2$^1$-[1,2-Ethanediylbis[Imino(1-Methyl-2,1-Ethanediyl)]]-Bis [5-Nitro-1H-Benz [DE] Isoquinoline-1,3-(2H)-Dione] Dimethanesulfonate (DMP 840) Cancer Res 54 (1994) pp. 2199–2206.
Goodgame et al., "Metal Complexes of Ligands Containing Intercalating Units," *Chemical Abstracts,* 115(4):801, Jul. 1991.
PCT Search Report, Jul. 24, 1995.
Arthaud et al., "Preclinical toxicity of the anticancer agent DMP 840 in mice, rats and dogs," *Proc. Amer. Assoc. Cancer Res.,* 34:384. Abstract 2290, 1993.
Bousquet et al., "Bis–naphthalimides demonstrate significant antitumor activity in vivo," *Proc. Amer. Assoc. Cancer Res.,* 34:374. Abstract 2230, 1993.

Braña et al., "Bis–naphthalimides, a novel class of antitumor agents," *Proc. Amer. Assoc. Cancer Res.,* 34:383. Abstract 2285, 1993.
Chen et al., "Effects of a bis–naphthalimide anti–cancer agent XB596 on cell cycle kinetics of MCF-7 human breast tumor cells," *Proc. Amer. Assoc. Cancer Res.,* 34:348. Abstract 2074, 1993.
Chen et al., "XB596, a promising bis–naphthalimide anti–cancer agent," *Anti–Cancer Drugs,* 4:447–457, 1993.
Cornbleet et al., "Mitoxantrone for the Treatment of Advanced Breast Cancer: Single-agent Therapy in Previously Untreated Patients," *Eur. J. Cancer Clin. Oncol.,* 20:1141–1146, 1984.
Czerniak et al., "Magnitude and duration of anti–tumor response caused by DMP 840, a novel bis–naphthalimide anti–tumor agent, against human solid tumor xenografts in vivo," *Proc. Amer. Assoc. Cancer Res.,* 34:384. Abstract 2289, 1993.
Hsiang et al., "Topoisomerase II–Mediated DNA Cleavage by Amonafide and Its Structural Analogs," *Molec. Pharmcol.,* 36:371–376, 1989.
McRipley et al., "Evaluation of DMP 840, a novel anti–tumor agent, in murine and human tumor models *in vivo,*" *Proc. Amer. Assoc. Cancer Res.,* 34:384. Abstract 2291, 1993.
Papp et al., "Mechanistic and anti–proliferative activities of DMP 840, a novel bis–naphthalimide anti–tumor agent," *Proc. Amer. Assoc. Cancer Res.,* 34:384. Abstract 2288, 1993.
Qian et al., "Bis–naphthalimides bind strongly to DNA and inhibit topoisomerase II but do not stabilize topoisomerase II/DNA cleavable complexes," *Proc. Amer. Assoc. Cancer,* 34:426. Abstract 2542, 1993.
Stafford et al., "DNA binding characteristics of DMP 840, a novel bis–naphthalimide anti–tumor agent," *Proc. Amer. Assoc. Cancer Res.,* 34:384. Abstract 2292, 1993.
Sun et al., "Synthesis and anti–proliferative properties of novel bis–naphthalimides, CMP 840 and its stereoisomers," *Proc. Amer. Assoc. Cancer Res.,* 34:384. Abstract 2287, 1993.

(List continued on next page.)

*Primary Examiner*—Ralph J. Gitomer
*Attorney, Agent, or Firm*—Arnold, White & Durkee

[57] ABSTRACT

The present invention provides novel bis-naphthalimides characterized by having a linker containing a heteroatom, their preparation, pharmaceutical compositions thereof, and various methods of using the bis-naphthalimides. Particularly preferred bis-naphthalimides have a linker of about 8–16 atoms where the heteroatom is oxygen, sulfur, sulfur oxide or sulfur dioxide. The bis-naphthalimides provided herein have exceptional DNA binding properties and demonstrate cytotoxicity in both in vitro and in vivo tumor models, in particular, against melanoma. Also provided a novel mono-naphthalimides linked to a DNA alkylating agent. These agents are shown to have conformational effects on double stranded DNA and to form covalent adducts after an extended incubation period.

2 Claims, 4 Drawing Sheets

OTHER PUBLICATIONS

Talbot et al., "Anthrapyrazole CI941: A Highly Active New Agent in the Treatment of Advanced Breast Cancer," *J. Clin. Oncol.*, 9:2141–2147, 1991.

Berners-Price, "Stereospecific Hydrogen-Bonding in Mononucleotide Adducts of Platinum Anticancer Complexes in Aqueous Solution," *J. Am. Chem. Soc.*, 115:8649–8659, 1993.

Bowler and Lippard, "Modulation of platinum antitumor drug binding to DNA by linked and free intercalators," *Biochemistry*, 25:3031–3038, 1986.

Denny and Baguley, "Acridine-based anticancer drugs," *Molecular Aspects of Anticancer Drug-DNA Interactions*, vol. 2, chapter 7 (Neidle and Waring, eds.), CRC Press, Boca Raton, FL, 1994.

Farrell, N., "Nonclassical Platinum Antitumor Agents: Perspectives for Design and Development of New Drugs Complementary to Cisplatin," *Cancer Invest.*, 11(5):578–589, 1993.

Gean et al., "Preparation, characterization and the anticancer activity of a novel series of triaminemonochloroplatinum(II) cations linked to anthraquinone intercalators," *Eur. J. Med. Chem.*, 26:593–598, 1991.

Kraker et al., "Anticancer Activity in Murine and Human Tumor Cell Lines of Bis(platinum) Complexes Incorporating Straight-Chain Aliphatic Diamine Linker Groups," *J. Med. Chem.*, 35:4526–4532, 1992.

Gibson et al., "Preparation, Characterization and Anticancer Activity of a Series of cis-$PtCl_2$ Complexes Linked to Anthraquinone Intercalators," *J. Med. Chem.*, 34:414–420, 1991.

McKeage and Kelland, "New Platinum Drugs," *Molecular Aspects of Anticancer Drug-DNA Interactions*, vol. 1, chapter 6 (Neidle and Waring, eds.), CRC Press, Boca Raton, Fl, 1993.

Lee et al., "DNA-Directed Alkylating Agents. 5. Acridinecarboxamide Derivatives of (1,2-Diaminoethane) dichloroplatinum(II)," *J. Med. Chem.*, 35:2983–2987, 1992.

Palmer et al., "Synthesis, DNA binding interactions and biological activity of bis-platinum(II) complexes of N,N,N',N'-tetrakis(2-aminoethyl)diamines," *Anti-Cancer Drug Design*, 7:385–401, 1992.

Roberts et al., "Interaction of novel bis(platinum) complexes with DNA," *Nucl. Acids Res.*, 17(23):9719–9733, 1989.

Sundquist et al., "Synthesis, Characterization and Biological Activity of cis-Diammineplatinum(II) Complexes of the DNA Intercalators 9-Aminoacridine and Chloroquine," *J. Am. Chem. Soc.*, 112:1590–1596, 1990.

Webster et al., "cis-Bis(pyridine)platinum(II) Organoamides with Unexpected Growth Inhibition Properties and Antitumor Activity," *J. Med. Chem.*, 35:3349–3353, 1992.

Woynarowski et al., "Effects on isolated and intracellular DNA of AB018, a novel cytotoxic drug with DNA alkylating, groove binding, and intercalating moieties," *Fifth International Congress on Anti-cancer Chemotherapy*, Paris, France, Jan. 31–Feb. 3, 1995.

Woynarowski et al., "Effects on isolated and intracellular DNA of AB018, a novel cytotoxic drug with DNA alkylating, groove binding, and intercalating moieties,"Abstract for poster presentation for *Fifth International Congress on Anti-cancer Chemotherapy*, Paris, France, Jan. 31–Feb. 3, 1995.

Yamashita et al., "Cytotoxicity of Platinum(IV) and Platinum(II) Complexes Containing 1R,2R-Cyclohexanediamine as a Ligand," *Biol. Pharm. Bull.*, 16(10):1014–1018, 1993.

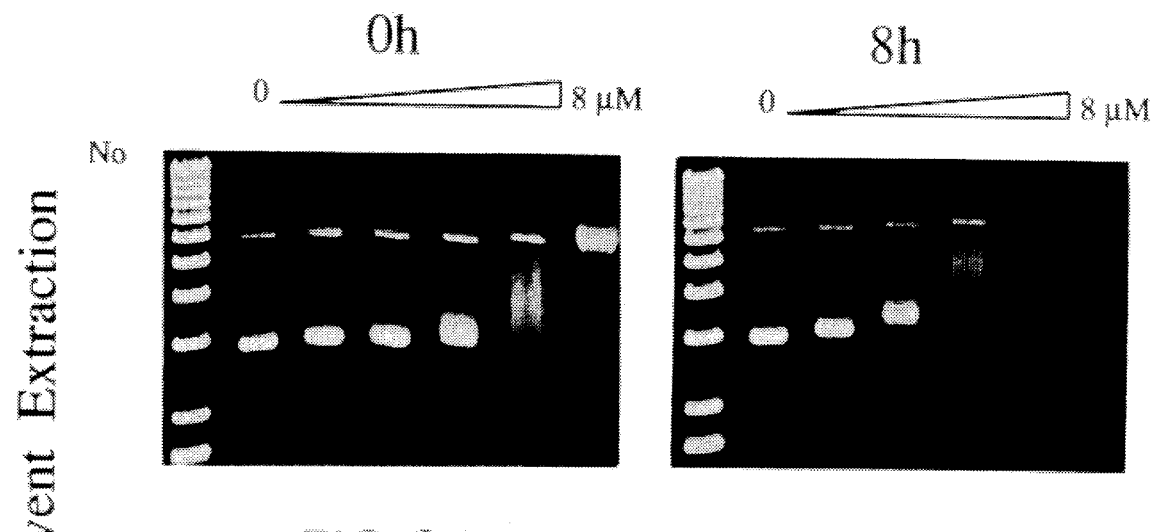
FIG.3A      FIG.3B
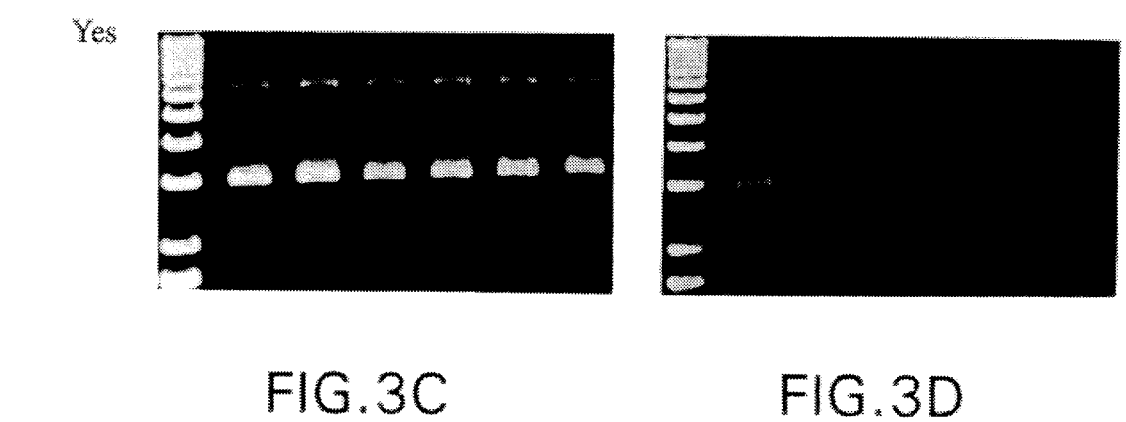
FIG.3C      FIG.3D

DIAMINE PLATINUM NAPHTHALIMIDE COMPLEXES AS ANTITUMOR AGENTS

This application is a continuation-in-part of copending application Ser. No. 08/279,173, filed Jul. 22, 1994. The entire text and figures of the above-referenced disclosure is specifically incorporated herein by reference without disclaimer.

BACKGROUND OF THE INVENTION

1. Field of the Invention

This invention relates to bis-naphthalimides having heteroatom linkers, processes for their preparation, pharmaceutical compositions thereof, and various methods of using such bis-naphthalimides.

2. Description of the Related Art

Bis-naphthalimides have generally been useful in electrophotographic processes, as dyes, as fluorescent probes, in protein immobilization, in the stabilization of lipid bilayers or micelles, in organism death, for viral inactivation, for encapsulation and more recently in the treatment of cancer.

Bis-naphthalimides contain two naphthalimide groups joined by a linker and are generally synthesized by reacting two identical or different 1,8-naphthalic anhydrides with a bis-amine. The bis-amine may have internal alkyl or heteroatom groups which form the linker between the two naphthalimide groups in the bis-naphthalimide. Known linkers include the following:

i) $C_4$–$C_{10}$ alkyl interrupted by one or two secondary or tertiary amino groups and two amino groups may be connected by an alkyl group, (U.S. Pat. No. 4,874,863, incorporated by reference herein);

ii) connected in order: $C_2$–$C_5$ alkyl; quaternary amine or nitrogen substituted cyclohexyl; methylene, methylene-carbonyl, methylene-amide, or methylene-amide-methylene; benzyl or dibenzyl coupled by methylene, isopropylene, oxygen or sulfur dioxide; this half of the linker is then repeated in reverse order for the other half of the linking group (U.S. Pat. No. 4,841,052, incorporated by reference herein);

iii) connected in order: alkyl or derivatized alkyl; carbonyl or thiocarbonyl; tertiary amine; —$(CH_2)_n$— n is 0 or 2–12; tertiary amine; carbonyl or thiocarbonyl; alkyl or derivatized alkyl (U.S. Pat. No. 5,206,250, incorporated by reference herein);

iv) connected in order: $C_2$–$C_{10}$ alkyl, tertiary amine, $C_2$–$C_{10}$ alkyl, tertiary amine, $C_2$–$C_{10}$ alkyl (U.S. Pat. No. 5,086,059, incorporated by reference herein);

v) connected in order: alkyl; tertiary amine; alkyl; tertiary amine; alkyl (DMP840 is an example,U.S. Pat. No. 5,206,249, incorporated by reference herein);

vi) combinations of unsaturated or saturated alkyl, fluorinated alkyl, alicyclic, aryl derivatives thereof, substitutions thereof, groups capable of complexing a metal ion, and biomolecules (U.S. Pat. No. 5,235,045, incorporated by reference herein); and vii) connected in order: propylene, secondary amine, butylene (Chen et al., 1993).

Current treatment methods for cancer, including radiation therapy, surgery, and chemotherapy, are known to have limited effectiveness. For example, breast cancer kills tens of thousands of people annually in the United States, the number being surpassed only by lung cancer deaths. Even with the implementation of educational programs designed to curb smoking and eating habits, cancer mortality rates will remain high well into the 21st century. The morbidity and mortality associated with cancer is exacting an ever increasing financial toll on an already overburdened health system. The development of new therapeutic compounds for the treatment of cancer is, therefore, a very important goal.

DNA intercalating agents are one of the most widely used classes of cancer chemotherapeutic agents currently used for the management of human cancers. Doxorubicin and daunorubicin are anthracycline antibiotics that intercalate with DNA. Although they differ slightly in chemical structure, daunorubicin has been used primarily in the acute leukemias, whereas doxorubicin has broader activity against human neoplasms, including a variety of solid tumors. The clinical value of both agents is limited by an unusual cardiomyopathy (Calabresi and Chabner, 1990). Several intercalators, including amsacrine (Denny, 1983), mitoxantrone (Cornbleet, 1984), and the anthrapyrazole DuP 941 (Talbot, 1991) have been reported to exhibit clinical anti-tumor activity. The DNA intercalator amonafide, a mono-naphthalimide, was reportedly shown to inhibit topoisomerase II and to result in intercalator-stabilized-topoisomerase II-DNA clearable complex formation (Hsiang et al., 1989).

Bousquet et al. (1993) reported cytotoxic activity in vitro and in vivo for certain bis-naphthalimides and Brana et al. relate to certain bis-naphthalimides having activity on a broad spectrum of human cancer cell lines. Chen et al. (1993) describe the synthesis of a bis-naphthalimide, XB596, having the linker—$(CH_2)_3$—NH—$(CH_2)_4$—. This compound reportedly demonstrated in vivo anti-tumor activity against MX-1 human breast carcinoma and DLD-2 human colon adenocarcinoma. However, its poor water solubility (45 mg/l) precluded further development (Sun et al., 1993).

DMP840, (R,R)-2,2′[1,2-ethanediylbis[imino (1-methyl-2,1 -ethanediyl)]]-bis[5-nitro-1H-benz[de]isoquinoline-1,3-(2H)-dione]dimethanesulfonate, is in phase I clinical trials (Sun et al., 1993; Papp et al., 1993; Czerniak et al., 1993; Arthaud et al., McRipley et al., 1993; Stafford et al., 1993). It has a reported water solubility of 3.4 g/l, anti-tumor efficacy in vivo, in particular against solid tumor xenografts, human and murine leukemia, doxorubicin resistant cell lines, colon carcinoma cells, early- and up-staged MX-1 mammary tumors, DLD-2 colon tumors, LX-1 lung carcinoma with no irreversible toxicities.

Although many of the compounds described above have general anti-cancer properties, most are ineffective against melanoma; in particular, the bis-naphthalimide, XB596, is ineffective against B16 melanoma (Chen et al., 1993)

SUMMARY OF THE INVENTION

The present invention seeks to solve problems inherent in the prior art by providing novel bis-naphthalimide compounds that are particularly effective anti-tumor agents. Pharmaceutical compositions including these compounds are effective in vivo against breast cancer, colon cancer and B16 melanoma. This invention also provides processes for the preparation of these compounds, pharmaceutical compositions containing these compounds, methods of using these compounds, e.g., for killing malignant cells, treating cancer in mammals and for visualizing DNA.

Although certain bis-naphthalimides having anti-tumor activity have been previously described, the present inventors have been able to synthesize bis-naphthalimides having heteroatom linkers that have anti-tumor activity against B16 melanoma that far exceeds the efficacy of the prior art compounds. The present invention addresses a particular need in the field of melanoma treatment since compounds provided herein have particular effectiveness against melanoma.

While not wishing to be bound by any particular theories, it is believed that the efficacy of these novel compounds may be related to the linkers of the present invention having more flexibility in interactions with DNA. For example, the bis-naphthalimides having a linker with one nitrogen and one oxygen or sulfur are more flexible than the corresponding bis-naphthalimide with two nitrogens in its linker. It is also contemplated that this structural change has unexpected ramifications on the chemistry of the bis-naphthalimide. By way of example, the bis-naphthalimide containing oxygen or sulfur in its linker has an altered hydrogen bonding ability compared to the corresponding bis-naphthalimide with two nitrogens in its linker. Therefore, it may have a completely different profile of interactions with the phosphodiester backbone of the DNA which clearly will change the biological activity of these compounds.

The bis-naphthalimides provided by the present invention are represented by formula (i). Generally, the ring substituted groups, i.e., U, V, Y and Z, may separately and independently be any of a wide variety of substituents, including hydrogen, nitro, amine, hydroxyl, alkoxy, halogen, trihalomethyl, alkyl, aryl, formyl, alkylcarbonyl, ureyl, alkylureyl or alkylcarbonylamino. However, it is preferred to have at least one of the ring substituents be a nitro group.

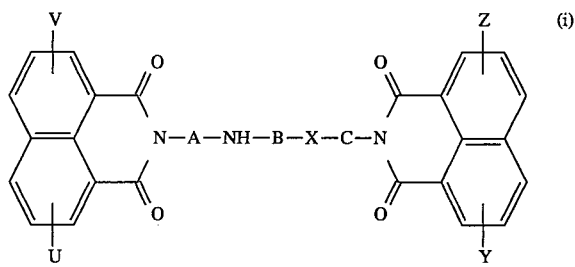

An important aspect of the invention is the construction of the linker connecting the naphthalimide moieties. The inventors have found that certain novel linker constructs allow more flexible interactions with DNA. The use of these new linker constructs in bis-naphthalimides dramatically improves their biological activity. It is contemplated that the use of certain heteroatoms, in combination with an optimum chain length, may provide increased potency against several cancers. Thus, for example, the A, B and C segments will typically range from 2–4 carbon atoms in the chain so that total chain length will be between about 8 to about 16 atoms. The heteroatom X moiety may be oxygen or sulfur or an oxide of the heteroelement, e.g., SO, $SO_2$, or NO. Active compounds are also provided where X is NHCONH, NHCSNH, NHC(NH)NH, or $NR_1NR_2$, where $R_1$ and $R_2$ are separately and independently hydrogen, lower alkyl, and aryl. Lower alkyl refers to branched and straight chained $C_1$–$C_5$ alkyls. It is contemplated that X may also be Se or P, as these atoms are similar to other heteroatoms employed.

Preferred compounds of the present invention in view of their anti-cancer activity are those compounds of formula (i) with linkers having one nitrogen and one oxygen or SO in their structure. These compounds where A, B, and C are —$CH_2CH_2$—, U and Y are a nitro group in the 3 position, and V and Z are hydrogen are preferred. Compound 6 is particularly preferred for its in vivo activity against B16 melanoma.

Bis-naphthalimides having a formula similar to formula (i) but having two oxygens in their linker are also encompassed by the present invention; that is, oxygen is substituted in formula (i) in place of X and NH. A preferred embodiment of this aspect of the present invention are those compounds having two oxygens in their linker where A, B, and C are —$CH_2CH_2$—, U and Y are a nitro group in the 3 position, and V and Z are hydrogen.

In a second respect, this invention is a compound, or a pharmaceutically acceptable salt thereof, of formula (ii):

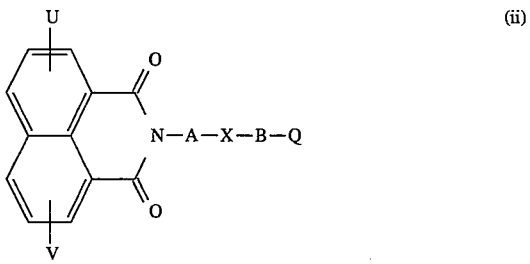

wherein X is CH, O, S, SO, $SO_2$, NO, $NR_1R_2$, NHCONH, NHC(NH)NH, or NHCSNH; wherein $R_1$ and $R_2$ are separately and independently hydrogen, alkyl of from one to five carbons or aryl of up to 20 carbons; wherein A and B are independently alkyl having a straight chain component of 2–4 carbon atoms where each carbon atom is bonded to H, a heteroatom or an alkyl or alkenyl having up to V carbon atoms; wherein U and V are separately and independently hydrogen, nitro, amine, hydroxyl, alkoxy, halogen, trihalomethyl, alkyl, aryl, formyl, alkylcarbonyl, ureyl, alkylureyl or alkylcarbonylamino; and wherein Q is a diamine complexed with platinum. A preferred embodiment is a compound of similar to formula (ii), wherein A and B are each ethylene, X is NH and Q is (—NH—$CH_2CH_2$—$NH_2$)Pt(II)$Cl_2$.

In this second respect of the compounds of this invention, the compound contains single naphthalimides ("mononaphthalimides") bonded to a linker that contains a diamine that can form a complex with platinum. The mononaphthalimides are of the formula (ii), described hereinabove. In formula (ii), Q is preferably —NH—$CH_2CH_2CH_2$—$NH_2$ or —NH—$CH_2CH_2$—$NH_2$ which is complexed with platinum. The platinum can be Pt(II) or Pt(IV), with Pt(II) being preferred. The platinum is also complexed with additional ligands in either the cis or trans configuration, with the cis configuration being preferred. Representative examples of suitable additional platinum ligands include amine ($NH_3$), amines of one to twelve carbons such as ethylamine, pyridine, pyrimidine, aniline, purine and cyclohexylamine, diamines such as ethylenediamine, 2,2'-bipyridine and 1R,2S-cyclohexanediamine, hydroxy, chloro, anionic derivatives of carboxylic acids of from one to six carbon atoms such as acetic acid and 2-hydroxy-1-propanoic acid ($CH_2$—CHOH—COOH) and anionic derivatives of dicarboxylic acids of from one to six carbon atoms such as oxalic acid (HOOC—COOH) and 1,1-dicarboxycyclobutane. In one embodiment, Q is (—NH—$CH_2CH_2$—$MH_2$)Pt(II)$Cl_2$. The platinum can be complexed with the mononaphthalimides using conventional techniques. A representative experimental procedure for such preparations is shown in an Example, hereinafter. Also in the examples, hereinafter, it is demonstrated that the mononaphthalimides exhibit useful biological activity in both inhibition of tumor cell growth and in DNA binding.

The inventors have found that the novel bis-naphthalimides described herein exhibit cytotoxicity both in vitro and in vivo towards several types of tumors. As such, they are desirably formulated as pharmaceutical compositions of various forms suitable for convenient administration. There are many convenient formulations that allow one of skill in the art to choose among the most suitable for the particular case, as for example administration to an elderly patient where slow release formulations might be preferred. In any event, the particular situation will be analyzed by competent personnel trained in cancer treatment.

In some forms, it will be desirable to formulate the novel compounds in salt form, generally to improve the solubility and bioavailability and to provide an active drug form more readily assimilated. As used herein, the term "pharmaceutically acceptable salt" refers to compounds which are formed from acidifying a solution of the compound of formula (i) with suitable physiologically tolerated acids. Suitable physiologically tolerated acids are organic and inorganic acids, such as hydrochloric acid, sulfuric acid, phosphoric acid, acetic acid, citric acid, oxalic acid, malonic acid, salicylic acid, maleic acid, methane sulfonic acid, isethionic acid, lactic acid, gluconic acid, glucuronic acid, amidosulfuric acid, benzoic acid, tartaric acid and pamoaic acid. Typically, such salt forms of the active compound will be provided or mixed prior to use with a physiologically acceptable solvent such as water or ethanol.

The bis-naphthalimides of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the bis-naphthalimides may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent, methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

The bis-naphthalimides may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the bis-naphthalimides in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with a bis-naphthalimide of the present invention, its use in the therapeutic compositions is contemplated. Supplementary active ingredients can also be incorporated into the compositions. Suitable pharmaceutical carriers are described in *Remington's Pharmaceutical Sciences*, Mack Publishing Company, a standard reference text in this field.

The pharmaceutical compositions of the present invention include the herein described formulations that include therapeutically effective amounts of the novel bis-naphthalimides. As used herein, the term "therapeutically effective tumor-inhibiting amount" refers to the dosage of the bis-naphthalimide compound required to produce the desired effect of inhibiting tumor growth. The dosage administered will be a tumor-inhibiting amount of active ingredient and will, of course, vary depending upon known factors, such as the pharmacodynamic characteristics of the particular active ingredient, and its mode and route of administration; age, health, and weight of the recipient; nature and extent of symptoms; concurrent treatment, if any; frequency of treatment; and the desired effect. While the general range of suitable doses will vary, such amounts may be readily determined by those skilled in the art, using methods similar to those described by the inventors; that is, ascertaining toxicity levels and optimum levels for therapeutic effect. All such determinations are well within the range of methods and procedures employed by those who work in the pharmaceutical sciences.

It will be appreciated that there will be significant variation in dosage forms, depending on the factors mentioned; however, as a general consideration, dosage forms (compositions) suitable for internal administration will typically contain from about 1.0 milligram to about 500 milligrams of bis-naphthalimide per unit. In these pharmaceutical compositions, the active ingredient will ordinarily be present in an amount of about 0.05–95% by weight based on the total weight of the composition.

Also encompassed by the present invention are methods of treating mammalian tumors. The methods comprise the step of administering a tumor-inhibiting amount of a compound of formula (i) to a mammal in need of therapy. The novel naphthalimides are active against human breast cancer, colon cancer and leukemia. An unexpected effect in vivo was observed against melanoma B16, a result not obtained with other reported naphthalimides. In particular, compound 6 was surprisingly more effective against B16 melanoma compared with DMP840, a known compound currently in clinical trials. The inventors contemplate that compound 6 and structurally related species will be effective against other melanomas as well as other sarcomas and carcinomas. Additionally, this class of novel compounds appears to have activity against a range of tumors, suggesting that activity will be found in breast cancer, colon cancer and leukemia, all related to the breast cancer, colon cancer and leukemia types tested. While the leukemia model system is a murine leukemia, one would expect activity against human leukemias because there is ample historic data demonstrating that a number of agents active against murine leukemias are also active against leukemia in humans.

The antitumor compounds of this invention can be administered to kill tumor cells by any means that allows contact of the active ingredient with the agent's site of action in the tumor. They can be administered by any conventional means available for use in conjunction with pharmaceuticals, either as individual therapeutically active ingredients or in a combination of therapeutically active ingredients. They can be administered alone but are generally administered with a pharmaceutically acceptable carrier selected on the basis of the chosen route of administration and standard pharmaceutical practice.

Also included in the scope of the present invention is a method of visualizing DNA. The method comprises the steps of: incubating DNA with a bis-naphthalimide having a structure shown in formula (i) or (ii) and visualizing the DNA by transillumination. The term "visualizing" refers to detecting the presence of DNA by spectroscopically measuring absorbance of a compound attached to the DNA. In the present case, the bis-naphthalimides will bind to DNA, causing a shift in ultraviolet absorption wavelength, thus indicating presence of native DNA.

One skilled in the art will recognize in light of the present disclosure that although the specified materials and conditions are important in practicing the invention, unspecified materials and conditions are not excluded as long as they do not prevent the benefits of the invention from being realized.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3A. Agarose gel demonstrates the effect of compound 21 on SV40 DNA with no incubation.

FIG. 3B. Agarose gel demonstrates the reversal of compound 21 on SV40 DNA by removal of compound 21 with phenol/chloroform extraction in 0.5M NaCl.

FIG. 3C. Agarose gel demonstrates effect of compound 21 on SV40 DNA after several hours incubation.

FIG. 3D. Agarose gel demonstrates no change in mobility after phenol/chloroform, 0.5M NaCl extraction of incubated DNA/compound 21.

DETAILED DESCRIPTION OF THE PREFERRED EMBODIMENTS

Figure 1:
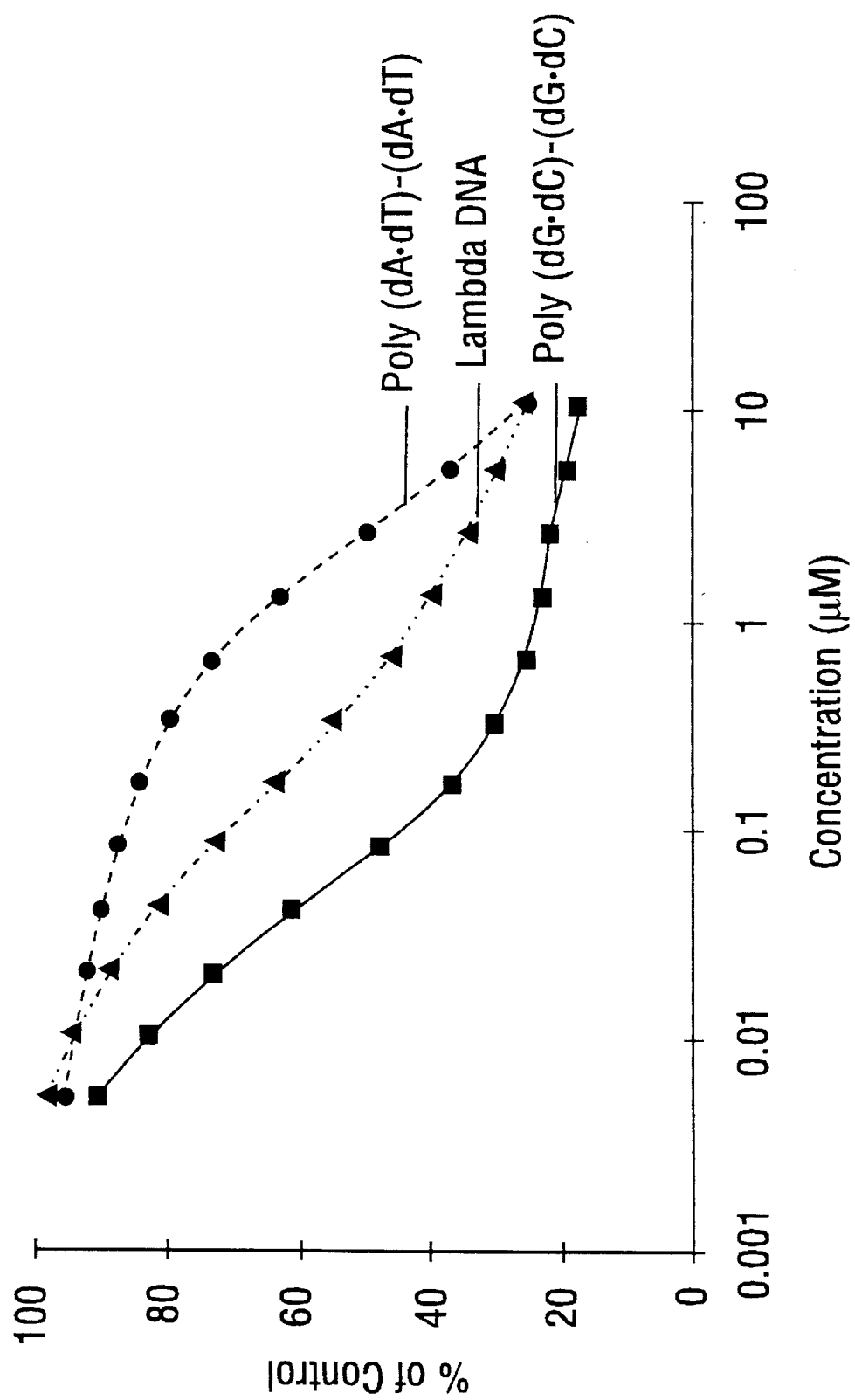
FIG. 1. Displacement of ethidium bromide by compound 6.

The present invention provides polyfunctional DNA interactive bis-naphthalimides as novel anticancer agents. The underlying concept involves a versatile synthetic scheme in which heterocyclic chromophores are attached to one or both ends of a straight chain linker region. Careful selection of both the nature and length of the linker atoms allows specific interaction of this portion of the molecule with the DNA backbone. The heterocycles, which are decorating the ends of the linker, are free to interact with regions of the DNA and/or processing enzymes. This concept provides modeling strategies for the synthesis of a new generation of anticancer agents that have mono, di- and tri-functional points of interaction with DNA. Examples of the successful use of this approach, in which selected naphthalimide chromophores have been attached to a methylene-based heterogeneous linker molecule, are provided in the following examples. The compounds of the present invention have exceptional DNA binding properties and demonstrate potent in vitro cytotoxicity and excellent in vivo antitumor activity.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Synthesis

Generally, bis-naphthalimides of the present invention were synthesized by reacting two equivalents of an anhydride (ii) with one equivalent of a diamine linker compound (iii) in an inert solvent, such as ethanol, dimethylformamide, or tetrahydrofuran, and at a temperature range from ambient to the solvent's boiling temperature (Scheme A). The resulting suspension was filtered to give the free base or it was acidified with the appropriate mineral or organic acid to produce a salt that was isolated by filtration.

Scheme A.

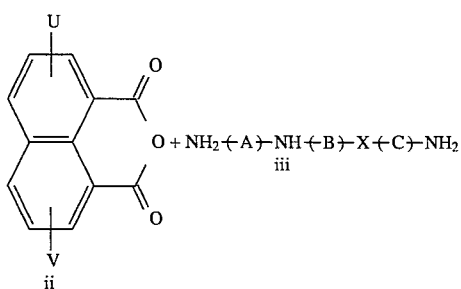

Appropriate anhydrides such as compound 4 shown in Step 2 of Scheme B are commercially available or are prepared according to procedures described in the literature (Hodgson, 1945). The various linker compounds were synthesized according to methods described below (Schemes B–E).

For compounds of Formula (i) where X=O (Scheme B), the amine compound 3 was used for the synthesis of the bis-naphthalimides (compounds 5 and 6). 1,8-diamino-3-oxa-6-azaoctane (3) was synthesized by reacting 2,2'-oxy-bis(ethyl amine)dihydrochloride (1), bromoethylamine hydrobromide (2), and sodium methoxide in ethanol. Condensation of compound 3 with the appropriate anhydride, e.g. compound 4, in ethanol at refluxing temperature yielded compound 5. The free base was further acidified with an appropriate acid, e.g. methane sulfonic acid, to yield the corresponding salt.

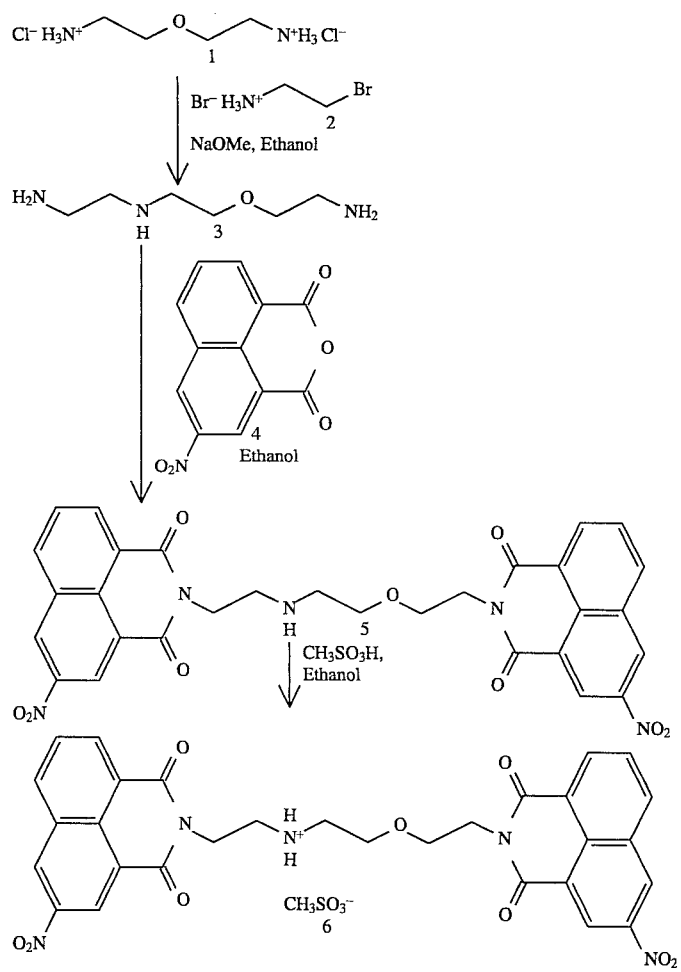

For compounds of Formula (i) where X=S (Scheme C), the amine compound 9 was used for the synthesis of the bis-naphthalimides (compounds 10 and 11). 1,8-diamino-3-thio-6-azaoctane (9) was synthesized by reacting a solution of 3-thio-6-azaoctanedinitrile (8) in tetrahydrafuran with lithium aluminum hydride and aluminum chloride in ether. The dinitrile 8 was synthesized by reacting 2-aminoethanethiol hydrochloride (7) in tetrahydrafuran with sodium hydride in dimethylformamide at room temperature for several hours. Condensation of compound 9 with the appropriate anhydride, e.g. compound 4, in ethanol at refluxing temperature yielded compound 10. The free base can be further acidified with an appropriate acid, e.g. with methane sulfonic acid, to yield the corresponding salt.

For compounds of Formula (i) where X=SO or $SO_2$ (Scheme D or E), the bis-naphthalimide compound 10 was oxidized with peracetic acid to form the sulfone or sulfoxide bis-naphthalimides (compounds 12 and 14). The free bases were further acidified with an appropriate acid, e.g. methane sulfonic acid, to yield the corresponding salts (compounds 13 and 15).

Scheme C.

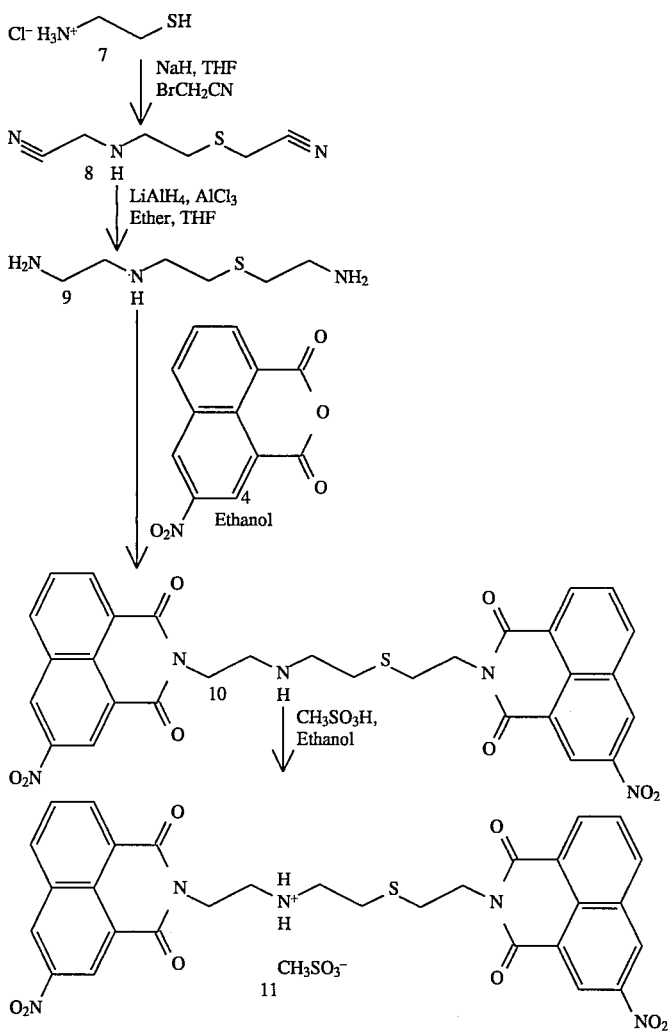

Scheme D.

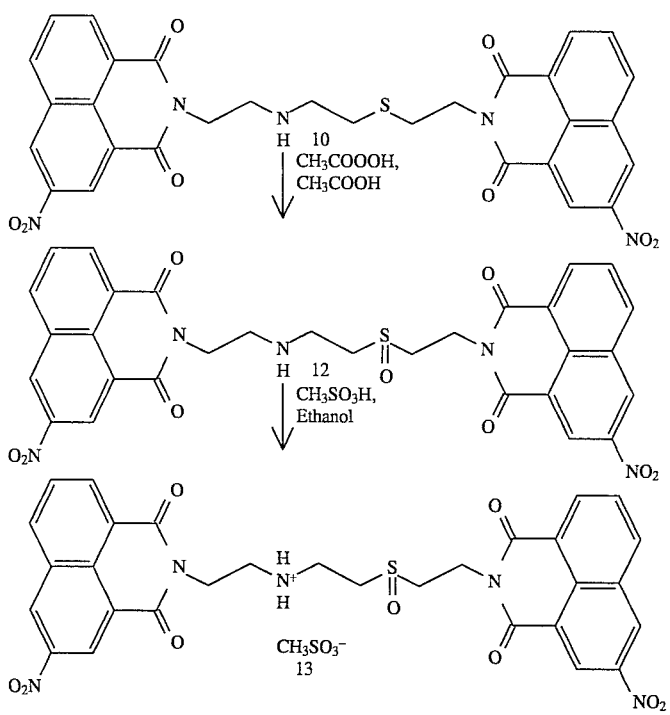

Scheme E.

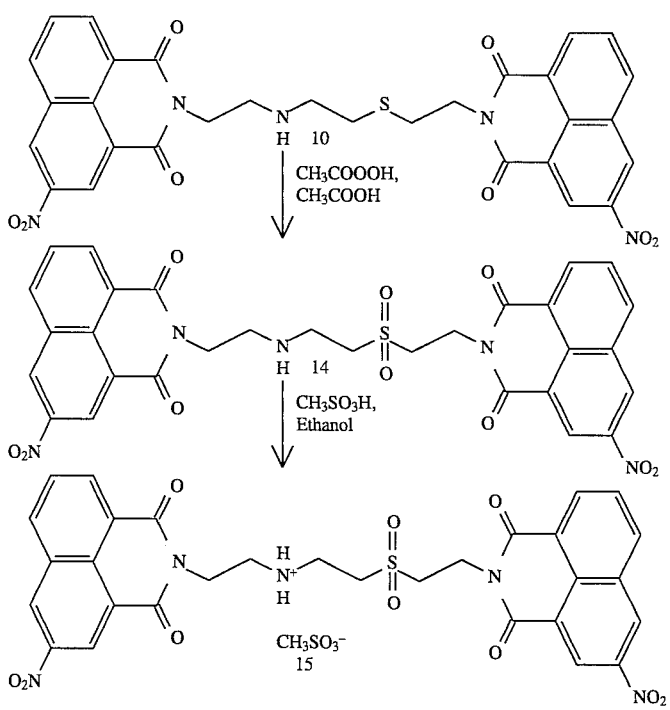

Compounds of the present invention having two oxygen atoms in their linker can be synthesized in a similar manner as described in Scheme F, the diamine, compound 18, was used for the synthesis of the bis-naphthalimide, compounds 19. 1,8-diamino-3,6-dioxaoctane (18) was synthesized by reacting a solution of 1,2-bis(2-azidoethoxy)ethane (17) in tetrahydrafuran with lithium aluminum hydride. The diazide 17 was synthesized by reacting 1,2-bis(2-chloroethoxy-)ethane (16) with sodium azide and Adogen 464, a phase transfer reagent, in water at 98° C. for sixteen hours.

Condensation of compound 18 with the appropriate anhydride, e.g. compound 4, in ethanol at refluxing temperature yielded compound 19.

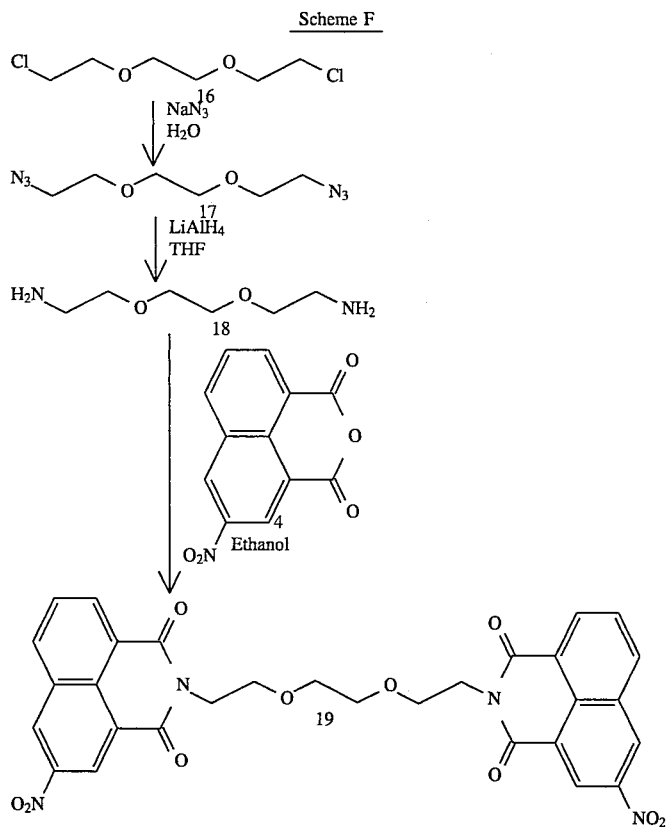

Scheme F

The known anticancer agents DMP840, cytoxan, and compound 022 were used as references for comparative purposes in determining the DNA binding ability and the in vitro and in vivo anticancer activities of the compounds of the present invention.

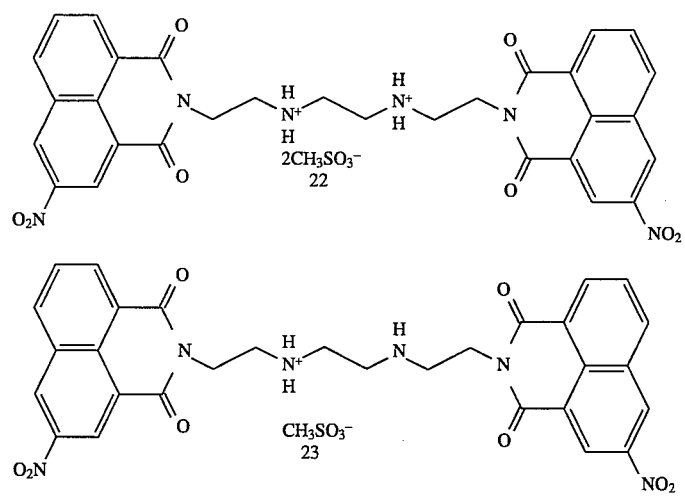

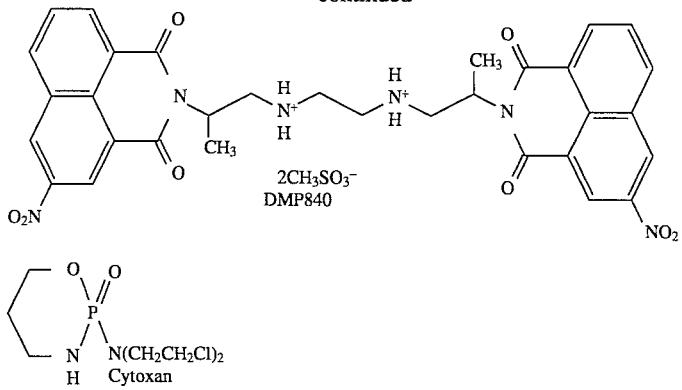

The synthesis of the known anticancer agent compound 22 and 23, 2,2'[1,2-ethanediylbis[imino(2,1-ethanediyl)]]-bis[5-nitro-1H-benz[de]isoquinoline-1,3-(2H)-dione] dimethanesulfonate and monomethanesulfonate, respectively, can be synthesized by the condensation of compound 4 with anhydrous tetraethylene triamine in refluxing toluene for sixteen hours, followed by acidification with methanesulfonic acid.

The biological activity of these bis-naphthalimides was determined using two in vitro model systems. The first system involved measuring the growth inhibitory activity of the compounds against various cultured murine and human tumor cells. The second involved determining the binding affinity of the compounds for DNA. In general, compounds that are very effective in both inhibiting tumor cell growth and in binding DNA exhibit good in vivo activity against tumors. However, it is also possible that compounds that are not effective at binding DNA will exhibit both in vitro and in vivo tumor inhibiting activities.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

The following examples are provided for purposes of clarification not limitation. One skilled in the art would recognize in light of the present disclosure that although the specified materials and conditions are important in practicing the invention, unspecified materials and conditions are not excluded as long as they do not prevent the benefits of the invention from being realized.

ABBREVIATIONS

DMSO: dimethylsulfoxide
EDTA: ethylenediaminetetraacetic acid
HZ: hertz
IR: infrared
J: coupling constant
NMR: nuclear magnetic resonance
PPM: parts per million ($\delta$)
TFA: trifluoroacetic acid

EXAMPLE 1

Synthesis and Characterization of Bis-Naphthalimides

The present example provides for the synthesis and characterization of bis-naphthalimides of the present invention.

All solvents and reagents were of reagent grade quality, available commercially from Spectrum Chemical Manufacturing Corporation or Aldrich Chemical Company, and were used without further purification unless otherwise mentioned. All reactions were performed in oven-dried glassware under an atmosphere of argon.

$^1$H and $^{13}$C NMR spectra were recorded on a Bruker AC 250 MHz Spectrometer. Chemical shifts were reported in parts per million ($\delta$, ppm) with reference to tetramethylsilane. $^1$H NMR coupling constants (J values) are listed in hertz (Hz) and spin multiplicities are reported as singlet (s), doublet (d), triplet (t), quartet (q), and multipier (m).

Rf's were determined by analytical thin layer chromatography (TLC). Rf refers to the relative flow of a particular compound versus the position of the solvent front on the TLC plate with reference to the initial spot where the sample was deposited. TLC was employed using precoated plates (silica gel, 60 F-254) and spots were visualized with ultraviolet light or iodine. Flash column chromatography was performed with silica gel (230–400 mesh, purchased from Whatman). Melting points (uncorrected) were determined with a Fisher-Johns melting point apparatus. IR spectra were recorded on a Bruker IFS 25 spectrometer.

The Electron Impact Ionization (EI) mass spectra were recorded on a Finnigan MAT 4615 mass spectrometer. Samples were introduced by means of a direct insertion probe. The ion source temperature was 160° C. The probe was heated ballistically to effect sample volatilization. Fast Atom Bombardment (FAB) mass spectra were acquired on a Finnigan MAT 212 mass spectrometer. The accelerating voltage was 3 kV and the ion source temperature was approximately 60° C. The Ion Tech Saddle Field atom gene was employed with xenon at a voltage 9 keV. Samples were applied in solution to the copper probe tip. Thioglycerol (2–3 μL) was then added and mixed with the sample. The contribution from the thioglycerol matrix was subtracted from each sample spectrum.

1,8-Diamino-3-oxa-6-azaoctane (3)

To a mixture of 2,2'-oxy-bis(ethylamine)dihydrochloride (1) (177 mg, 1 mmol), bromoethylamine hydrobromide (2) (204.9 mg, 1 mmol), in ethanol (10 mL) was added sodium methoxide (162.6 mg, 3 mmol) at room temperature. The reaction mixture was refluxed for 48 hours under a positive flow of argon. Reaction mixture was cooled to room temperature, ethanol was evaporated on rotavapor and the crude product (135 mg) was directly taken into next step to prepare the bis-naphthalimide, compound 5.

¹H NMR spectrum in DMSO-d$_6$ (units δ): 0.83 (m, 4H), 2.62 (m, 8H), 3.40 (m, 4H).

5-[2-(3-Nitronaphthalene-1,8-dicarboximido)ethylamino]-1-(3-nitronaphthalene-1,8-dicarboximido)-3-oxapentane (5)

Compound 3 (132 mg, 0.9 mmol) and 3-nitro 1,8-naphthalin anhydride 4 (437.4 mg, 1.8 mmol) were taken into ethanol (20 mL). The heterogenous mixture was stirred at reflux temperature (bath temperature 90°–100° C.) for 12 hours. The reaction mixture was cooled to room temperature. The separated solid was filtered, washed with water and ethanol, and dried to obtain the bis-naphthalimide, compound 5 (430 mg, 72% yield). Rf=0.42 (10% methanol-CH$_2$Cl$_2$). Melting point 205°–208° C.

¹H NMR spectrum in DMSO-d$_6$ (units δ): 2.68 (t, J=6, 2H), 2.72 (t, J=6, 2H), 3.48 (t, J=6, 2H), 3.64 (t, J=6, 2H), 4.05 (t, J=6, 2H), 4.2 (t, J=6, 2H), 7.94 (m, 4H); δ8.55 (m, 2H), 8.64 (m, 2H), 8.78 (d, J=2.3, 1H), 8.81 (d, J=2.3, 1H), 9.32 (d, J=2.25, 1H), 9.33 (d, J=2.25, 1H).

¹³C NMR spectrum in DMSO-d6 (units δ): 40.16, 40.49, 46.49, 48.25, 66.71, 70.74, 122.27, 122.37, 122.62, 122.75, 123.71, 123.81, 129.12, 129.24, 129.48, 129.58, 130.64, 130.68, 133.75, 133.86, 136.10, 136.2, 145.6, 162.13, 162.63.

5-[2-(3-Nitronaphthalene-1,8-dicarboximido)ethylamino]-1-(3-nitronaphthalene-1,8-dicarboximido)-3-oxopentane hydromethane sulfonate (6).

Methanesulfonic acid (114.2 mg, 1.188 mmol) was added to the stirred mixture of compound 5 (710 mg, 1.188 mmol), in ethanol (20 mL) at room temperature. The reaction mixture was refluxed for 90 minutes. The cooled reaction mixture was filtered to obtain the methanesulfonate salt, compound 6 (755 mg, 92% yield). Melting point 195° C. (dec).

¹H NMR spectrum in DMSO-d$_6$ (units δ): 2.27 (s, 3H), 3.2 (m, 4H), 3.75 (m, 4H), 4.30 (m, 4H), 8.06 (m, 2H), 8.51 (broad s, 1H, OH), 8.68 (m, 2H), 8.78 (m, 2H), 8.92 (d, J=2.3, 1H), 8.95 (d, J=2.3, 1H), 9.46 (d, J=2.3, 1H), 9.51 (d, J=2.3, 1H).

3-Thio-6-azaoctanedinitrile (8)

To a stirred mixture of 2-aminoethanethiol hydrochloride (7) (1.136 g, 10 mmol) in tetrahydrofuran (20 mL), sodium hydride (480 mg, 20 mmol) in dimethylformamide (2 mL) was added in portions over a period of 5 minutes. The reaction mixture was stirred at room temperature for 4 hours. Afterwards the reaction mixture was cooled to −78° C. and bromoacetonitrile (2.399 g, 20 mmol) in tetrahydrofuran was added dropwise at −78° C. The reaction mixture was allowed to warm to room temperature over a period of about 3 hours and then left at room temperature for 12 hours. The reaction was quenched slowly with water and the tetrahydrofuran and dimethylformamide were evaporated under vacuum on a rotavapor. The residue was taken in water and extracted with ether (4×20 mL). The combined ether extract was washed with brine, dried over Na$_2$SO$_4$, filtered, and the ether was evaporated in vacuo to afford crude residue. The residue was purified by flash silica gel column chromatography (eluted with methylene chloride, 2% methanol-methylene chloride) to afford pure compound 8 (780 mg, 50% yield). IR spectrum (Neat, cm$^{-1}$): 3324, 2926, 2243, 1715, 1668, 1557.

¹H NMR spectrum in CDCl$_3$ (units δ): 2.92 (m, 2H), 3.03 (m, 2H), 3.31 (s, 2H), 3.65 (s, 2H). Mass spectrum 156 (M+1), 155, 128, 69.

1,8-Diamino-3-thio-6-azaoctane (9)

To a stirred mixture of lithium aluminum hydride (400 mg, 10.42 mmol) in ether (130 mL), aluminum chloride (1.39 g, 10.42 mmol) was added in one portion and stirred for 15 min at room temperature. The reaction mixture was cooled to 0° C. and dinitrile 8 (720 mg, 4.65 mmol) in tetrahydrafuran (15 mL) was added dropwise. The reaction mixture was stirred at room temperature for 15 hours. The reaction mixture was cooled to 0° C. and quenched slowly with 30% potassium hydroxide (55 mL). The organic layer was separated and the aqueous layer evaporated in vacuo. The residue was taken in methanol and was filtered through a small plug of celite. The methanol filtrate and the above organic layers were combined, dried over Na$_2$SO$_4$, filtered, and the ether was evaporated on a rotavapor to obtain compound 9 (495 mg, 65% yield).

¹H NMR spectrum in CDCl$_3$ (units δ): 2.6 (m, 8H); 2.79 (m, 5H); 2.84 (m, 4H).

5-[2-(3-Nitronaphthalene-1,8-dicarboximido)ethylamino]-1-(3-nitronaphthalene-1,8-dicarboximido)-3-thiopentane (10)

A mixture of compound 9 (490 mg, 3 mmol) and 3-nitro-1,8-naphthalic anhydride (4) (1.46 g, 6 mmol) in ethanol (60 mL) was refluxed for 12 hours. The reaction mixture was cooled to room temperature and the solid was separated by filtration. The solid was washed with ethanol and dried in vacuo to afford the bis-naphthalimide, compound 10 (1.45 g, 80% yield). Rf=0.45 (10% methanol-CH$_2$Cl$_2$). Melting point 135°–138° C. IR spectrum (KBr, cm$^{-1}$): 3365, 3076, 2966, 1662, 1597, 1537.

¹H NMR spectrum in TFA-d (units δ): 3.01 (m, 2H), 3.10 (m, 2H), 3.59 (m, 2H), 3.82 (m, 2H), 4.52 (m, 2H), 4.81 (m, 2H), 7.99 (m, 2H), 8.55 (m, 2H), 8.85 (m, 2H), 9.31 (m, 2H), 9.34 (m, 2H).

5-[2-(3-Nitronaphthalene-1,8-dicarboximido)ethylamino]-1-(3-nitronaphthalene-1,8-dicarboximido)-3-thiopentane hydromethane sulfonate (11)

Methanesulfonic acid (144 mg, 1.5 mmol) was added to the stirred mixture of compound 10 (920 mg, 1.5 mmol) in ethanol (40 mL) at room temperature. The reaction mixture was stirred at reflux temperature (bath temperature 90°–100° C.) for 90 minutes. The reaction mixture cooled to room temperature and the solid was filtered, washed with ethanol, and dried in vacuo to afford the methanesulfonate salt, compound 11 (900 mg, 89% yield). Melting point 240°–245° C. (dec.).

¹H NMR spectrum in TFA-d (units δ): 2.93 (s, 3H), 3.03 (t, J=6.8, 2H), 3.13 (t, J=6.8, 2H), 3.62 (m, 2H), 3.97 (m, 2H), 4.52 (m, 2H), 4.78 (m, 2H), 7.50 (broad s, 1H, OH), 7.90 (m, 2H), 8.55 (m, 2H), 8.85 (m, 2H), 9.24 (d, J=2.1, 2H), 9.33 (d, J=2.1, 2H).

5-[2-(3-Nitronaphthalene-1,8-dicarboximido)ethylamino]-1-(3-nitronaphthalene-1,8-dicarboximido)-3-sulfonylpentane (12)

To a stirred solution of compound 10 (190 mg, 0.31 mmol), in acetic acid (6 mL), peracetic acid (23.5 mg, 0.31 mmol, 74 µL of 32 Wt % solution or 4.1M solution in acetic acid) was added at room temperature and stirred for 2 hours. The reaction mixture was diluted with ether (60 mL) and stirred at room temperature for 15 min. The separated solid was filtered, washed with ether, and dried in vacuo to afford pure compound 12 (151 mg, 77% yield).

Melting point 142°–146° C. (dec.). IR spectrum (KBr, cm$^{-1}$) 3329, 1700, 1604, 1541, 1422, 1333, 1247, 1107, 1045.

$^1$H NMR spectrum in TFA-d (units δ): 3.95 (m, 2H), 4.06 (m, 2H), 4.20 (m, 4H), 4.97 (m, 2H), 5.08 (m, 2H), 8.22 (m, 2H), 8.90 (m, 2H), 9.07 (m, 2H), 9.47 (m, 2H), 9.58 (m, 2H).

5-[2-(3-Nitronaphthalene-1,8-dicarboximido)ethylamino]-1-(3-nitronaphthalene-1,8 dicarboximido)-3-sulfonylpentane hydromethanesulfonate (13)

To a stirred solution of compound 12 (63 mg, 0.1 mmol) in ethanol (10 mL), methanesulfonic acid (9.6 mg, 0.1 mmol) was added at room temperature and the reaction mixture was refluxed for 90 minutes. The reaction mixture was cooled to room temperature. The solid was collected by filtration, washed with ethanol, and dried in vacuo to afford the methanesulfonate salt, compound 13 (55 mg, 76% yield). Melting point 240°–242° C. (dec.).

$^1$H NMR spectrum in TFA-d (units δ): 3.46 (s, 3H), 4.25 (m, 2H), 4.33 (m, 2H), 4.47 (m, 4H), 5.22 (m, 2H), 5.35 (m, 2H), 8.50 (m, 2H), 9.05 (m, 2H), 9.28 (m, 2H), 9.75 (m, 2H), 9.9 (m, 2H).

5-[2-(3-Nitronaphthalene-1,8-dicarboximidoethylamino]-1-(3-nitronaphthalene-1,8-dicarboximido)-3-sulfonylpentane (14)

Peracetic acid [157 mg, 0.70 mmol, 110 mg (346 µL) of 32 Wt % solution or 4.1 Molar solution in acetic acid] was added to compound 10 (201 mg, 0.33 mmol) in acetic acid (10 mL) at room temperature. The reaction mixture was stirred at room temperature for 24 h. Then the reaction mixture was diluted with ether (70 mL) and stirred at room temperature for 15 min. The solid was collected by filtration, washed with ether, and dried in vacuo to obtain compound 14 (160 mg, 75% yield). Melting point 185°–195° C. (dec.). IR spectrum (KBr, cm$^{-1}$): 3325, 3075, 1714, 1669, 1600, 1539, 1435, 1334, 1247, 1135.

$^1$H NMR spectrum in TFA-d (units δ): 4.10 (m, 8H), 4.90 (m, 4H), 8.14 (m, 2H), 8.65 (m, 2H), 8.98 (m, 2H), 9.40 (m, 4H).

5-[2-(3-Nitronaphthalene-1,8-dicarboximido)ethylamino]-1-(3-nitronaphthalene-1,8-dicarboximido)-3-sulfonylpentane hydromethanesulfonate (15)

Methanesulfonic acid (9.6 mg, 0.1 mmol) was added to compound 14 (64.6 mg, 0.1 mmol) in ethanol (10 mL) at 25° C. Then the reaction mixture was stirred at reflux temperature for 90 minutes. The reaction mixture was cooled to 25° C. and the solid was collected by filtration, washed with ethanol, and dried in vacuo to obtain the methanesulfonate salt, compound 15 (55 mg, 74% yield). Melting point 210°–212° C. (dec.).

$^1$H NMR spectrum in TFA-d (units δ): 3.49 (s, 3H); 4.47 (m, 8H), 5.30 (m, 4H), 8.49 (m, 2H), 9.05 (m, 2H), 9.31 (m, 2H), 9.75 (m, 4H).

EXAMPLE 2

Ethidium Bromide Displacement

The present examples demonstrates that bis-naphthalimides of the present invention intercalate with DNA. This is demonstrated by ethidium bromide displacement assays.
Stock Solutions.

A 10× Binding solution was prepared by combining 0.93 ml of an aqueous NaCl solution (5M), 2.0 ml of an aqueous Tris HCl (500 mM) solution, 0.1 ml of an EDTA solution (500 mM) and 46.97 ml of water. The resultant solution was 93 mM in NaCl, 20 mM in Tris HCl, and 1 mM in EDTA. Stock DNA solution were prepared as follows: Poly (dG·dC)–(dG·dC) (ε254=8.4/mM; 27 -7910-02), poly(dA·dT)–(dA·dT) (ε262=6.6/mM; 27-7870-02), and lambda DNA (ε260–7.0/mM; 27-4111-01) were purchased from Pharmacia. Solutions were prepared by resuspending either poly (dG·dC)–(dG·dC) or poly(dA·dT)–(dA·dT) in 1 ml of 10× DNA Binding Solution. Lambda DNA is already in solution as purchased.

Determination of concentration of the stock DNA solutions.

Poly (dG·dC)–(dG·dC), poly(dA·dt)–(dA·dt) and lambda DNA concentrations were determined as follows: 980 µl of 10× DNA Binding Solution was pipetted into a 1 ml cuvette. A blank was run on the UV spectrophotometer. 20 µl of the DNA stock of unknown concentration was then added into the cuvette. The sample was then scanned between 210 nm to 500 nm and the absorbance recorded at 254 nm for poly(dG·dC)–(dG·dC), at 262 nm for poly(dA·dT)–(dA·dT) and at 260 nm for lambda DNA. The solution was transferred to a clean tube. This procedure was followed for three different solutions with the absorbance taken as the average of the three. The concentration of poly(dG·dC)–(dG·dC) stock was calculated to be $A_{254}/8.4 \times 1000$ (in µM). The concentration of poly(dA·dT)–(dA·dT) stock was calculated to be $A_{262}/6.6 \times 1000$ (in µM). The concentration of lambda DNA stock was calculated to be $A_{260}/7.0 \times 1000$ (in µM).

Ethidium Bromide Displacement Assay.

The binding of the bis-naphthalimides to DNA and to synthetic polynucleotide duplexes was determined by an ethidium bromide displacement assay that measures the reduction of fluorescence when ethidium bromide is displaced from DNA (Baguley, 1981). The fluorescence intensity of a 3 ml solution containing 9.3 mM NaCl, 2 mM Tris-HCl (pH 7.0), 100 µM EDTA, 1 µM DNA (in nucleotides) and 1.26 µM ethidium bromide in a quartz cuvette was measured at the excitation (546 nm) and emission (600 nm) wavelengths on a Shimadzu RF5000U spectrofluorometer. Graded concentrations of agent were then added and the fluorescence intensity was measured. The concentration of compound required to reduce the fluorescence intensity by 50% of that of control (FI$_{50}$) was determined. Therefore, the lower the FI$_{50}$ the stronger the binding affinity a particular compound has for DNA.

The ability of bis-naphthalimides of the present invention and the known anti-cancer agents compound 22 and DMP840, (R,R)- 2,2'[1,2-ethanediylbis[imino(1-methyl-2, 1-ethanediyl)]]-bis[5 -nitro-1H benz[de]isoquinoline-1,3-(2H)dione]dimethanesulfonate, to bind to DNA and to synthetic oligonucleotide duplexes was measured using an ethidium bromide displacement assay. Ethidium bromide, a known DNA intercalator, has no fluorescence in the absence of DNA; however, fluorescence intensity increases when ethidium bromide binds to DNA. The ethidium bromide displacement assay measures the decrease in fluorescence intensity caused by DNA-bound ethidium bromide with DNA interacting agents. FIG. 1 shows a dose-dependent decrease in fluorescence intensity when graded concentrations of the bis-naphthalimide 6 of the present invention were added. Table 1 shows ethidium bromide displacement data for compounds 5, 10, 14, 12, 22 and DMP840.

TABLE 1

DNA Binding Affinity as Measured by an Ethidium Bromide Displacement Assay

| Compound | $FI_{50}$ (µM) | | | Ratio (AT/GC) |
|---|---|---|---|---|
| | Lambda DNA | poly (dG.dC) - poly (dG.dC) | poly (dA.dT) - poly (dA.dT) | |
| 5 | 0.241 | 0.071 | 5.22 | 73.5 |
| 10 | 7.37 | 0.77 | 17.2 | 22.3 |
| 14 | 24.18 | 0.672 | 43.26 | 64.38 |
| 12 | 0.169 | 0.125 | 6.383 | 51.06 |
| 13 | 0.18 | 0.018 | 3.848 | 212.6 |
| 15 | 1.027 | 0.118 | 17.087 | 144.4 |
| 22 | 0.053 | 0.048 | 0.787 | 16.5 |
| DMP840 | 0.073 | 0.092 | 3.283 | 35.2 |
| 21 | 0.235 | 0.239 | 0.173 | 0.72 |

In general, the compounds of the present invention bind very tightly and selectively to GC rich regions of DNA as indicated by the high AT/GC ratio. As compared to DMP840 and compound 22, the compounds of the present invention generally bind more selectively to GC rich regions and interact less strongly with DNA in general.

EXAMPLE 3

Bis-naphthalimides of the Present Invention Inhibit Cancer Cell Growth

The present example demonstrates that bis-naphthalimides of the present invention have activity against tumors in vitro. P388 murine leukemic cell line was obtained from the DCT Tumor Repository (National Cancer Institute, Frederick Cancer Research and Development, Frederick Md. 21702). HT29 Human Colon Carcinoma cell line was obtained from the American Type Culture Collection (12301 Parklawn Drive, Rockville, Md. 20852). B16 Melanoma cell line was obtained from DuPont Merck Pharmaceutical Company (Glenolden, Pa. 19036). MCF-7 Human Breast Carcinoma cell line was a gift from Dr. K. Osborne (Department of Medicine, The University of Texas Health Science Center at San Antonio, San Antonio, Tex. 78284). All cell lines were incubated at 37° C. in a humidified atmosphere of 5% $CO_2$-95% air. Murine B16 melanoma cell line was grown in RPMI 1640 medium supplemented with 10% heat-inactivated fetal bovine serum, 2 mM L-glutamine, 50 units/ml penicillin, 50 µg/ml streptomycin, 25 µg/ml gentamycin, 0.75% sodium bicarbonate, 10 mM HEPES buffer (pH 7.4), and 0.06 mg/ml AntiPPLO. Murine P388 leukemic and the human HT-29 colon adenocarcinoma cell lines were maintained in RPMI 1640 medium supplemented with 10% heat-inactivated fetal bovine serum. MCF-7M human breast adenocarcinoma was maintained in IMEM medium supplemented with 5% non heat-inactivated fetal bovine serum and 1 nM insulin.

Exponentially growing cells ($1-2\times10^3$ cells, unless specified otherwise) in 0.1 ml medium were seeded on day 0 in a 96-well microtiter plate. On day 1, 0.1 ml aliquots of medium containing graded concentrations of test compounds were added in duplicate to the cell plates. After incubation at 37° C. in a humidified incubator for 3 days (P388, B16) or 6 days (HT-29, MCF-7M), the plates were centrifuged briefly and 100 µl of the growth medium was removed. Cell cultures were incubated with 50 µl of 3-(4,5-dimethylthiazol-2-yl)-2,5-diphenyl-tetrazolium bromide [MTT, 1 mg/ml in Dulbecco's phosphate buffered saline (PBS)] for 4 hr at 37° C. The resulting purple formazan precipitate was solubilized with 200 µl of 0.04N HCl in isopropyl alcohol. Absorbance was monitored in a BioRad Model 3550 Microplate Reader at a test wavelength of 570 nm and a reference wavelength of 630 nm. The absorbance was transferred to a PC 486 computer. The $IC_{50}$ values were determined by a computer program (EZ-ED50) that fit all of the data to the following four-parameter logistic equation:

$$Y=((A_m-A_o)/(1+(X/IC_{50})^n))+A_o$$

where $A_m$ is the absorbance of control cells, $A_o$ is the absorbance of cells in the presence of highest agent concentration, Y is the observed absorbance, X is the agent concentration, $IC_{50}$ is the concentration of agent that inhibits the cell growth by 50% of control cells (based on the absorbance) and n is the slope of the curve.

Figure 2:
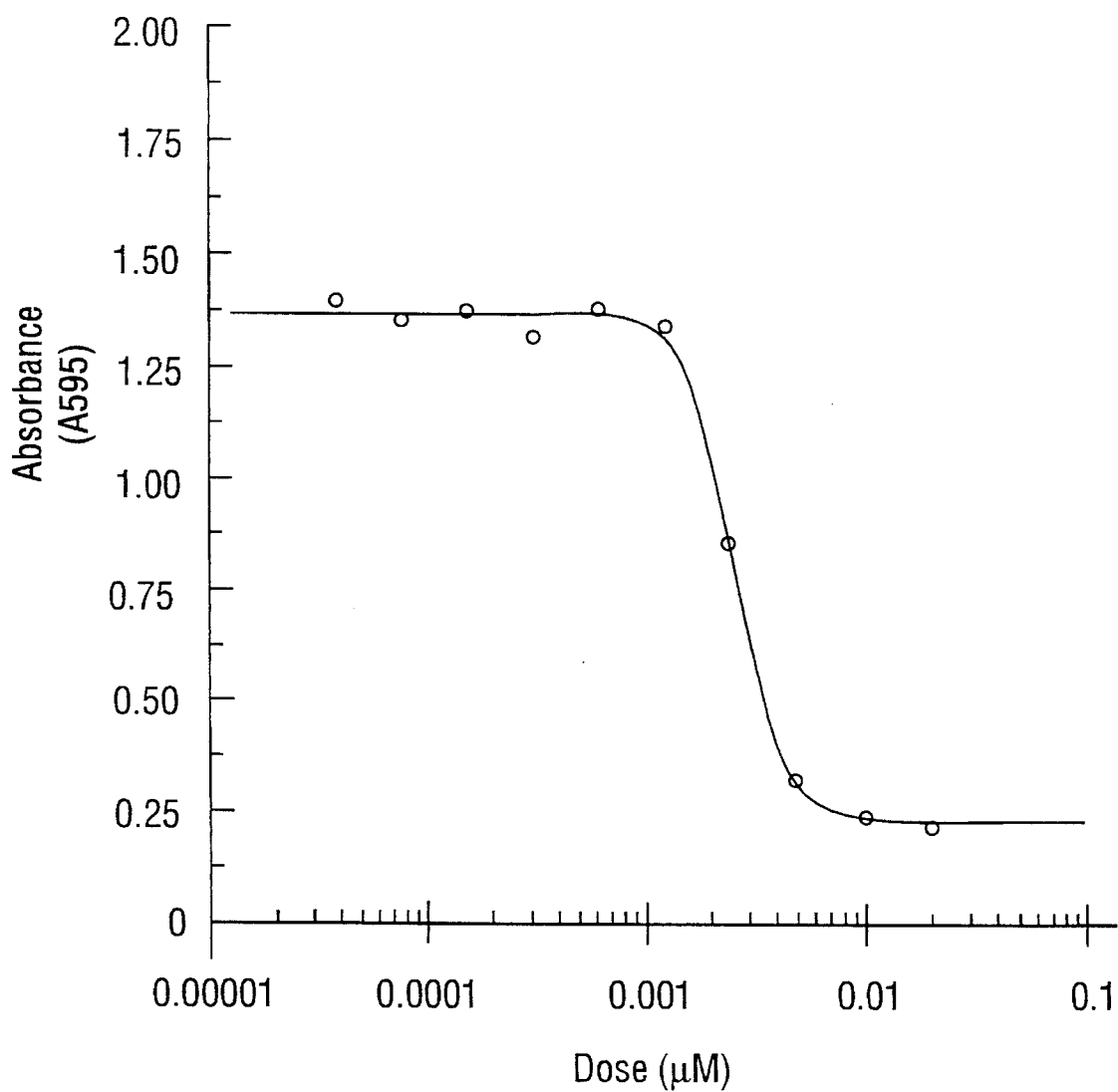
FIG. 2. Growth inhibitory activity of compound 6 against MCF- 7M.

The growth inhibitory activities of compounds of the present invention against several murine and human tumor cell lines were examined. A representative $IC_{50}$ determination for compound 6 is depicted in FIG. 2 and the results of the $IC_{50}$ determinations are summarized in Table 2.

TABLE 2

In Vitro Tumor Inhibiting Activity

| Compound | $IC_{50}$ (µM) | | | |
|---|---|---|---|---|
| | P388 | B16 | MCF-7 | HT29 |
| 5 | | 0.020 | 0.001 | 0.003 |
| 6 | 0.035 | 0.011 | 0.0026 | 0.003 |
| 10 | 0.0565 | 0.033 | 0.009 | |
| 14 | 0.027 | 0.086 | 0.132 | 0.044 |
| 12 | 0.009 | 0.0063 | 0.0016 | 0.0017 |
| 13 | <0.005 | 0.0016 | <0.0001 | 0.0002 |
| 15 | 0.0299 | 0.034 | 0.036 | 0.022 |
| 22 | | 0.0043 | 0.00053 | 0.00048 |
| 23 | 0.006 | 0.0129 | 0.00139 | 0.00052 |
| DMP840 | 0.006 | 0.027 | 0.007 | |
| 21 | 0.302 | 0.385 | 0.066 | 0.129 |

Many of these compounds potently inhibited the growth of mouse and human tumor cell lines. The results indicate that the compounds of the present invention have a very potent growth inhibitory activity against a variety of murine (leukemia P388, melanoma B16) and human (breast cancer MCF-7, colon carcinoma, HT29) tumors in vitro. These data also indicate the potential of the compounds of the present invention as anticancer agents in mammals.

EXAMPLE 4

In Vivo Tumor Inhibiting Activity

The present example demonstrates that bis-naphthalimides of the present invention, in particular, compound 6, has potent activity against B16 melanoma in vivo.
B16 Melanoma:

B6D2F1 mice received i.p. inocula of B16 murine melanoma brei prepared from B16 tumors growing subcutaneously in mice (day 0). On day 1, rumored mice were treated with drugs or vehicle control; the route of drug administration and schedule were selected as appropriate for the study in question. If dosing information for agents was not available, the maximum tolerated dose (MTD) was determined in initial dose finding experiments in non-tumored mice. In a typical experiment, drugs were given at their MTD and ½ MTD doses i.p. on a daily×5 schedule.

The mean survival times of all groups were calculated, and results were expressed as mean survival of treated mice/mean survival of control mice (T/C)×100%. A T/C value of 150 means that the mice in the treated group lived 50% longer than those of the control group; this is sometimes referred to as the increase in life space, or ILS value.

Mice that survived for 60 days were considered long term survivors, or cures, in the B16 model. The universally accepted cut-off for activity in this model, which has been used for years by the National Cancer Institute, is T/C=125. Conventional use of B16 over the years has set the following levels of activity: T/C<125, no activity; T/C=125–150, weak activity; T/C=150– 200, modest activity; T/C=200–300, high activity; T/C>300, with long term survivors, excellent, curative activity (Goldin et al., 1981).

Statistics were performed on the data using primarily the log rank p-value test.

In vivo studies showed that compounds of the present invention are active anti-cancer agents. An unexpected result was the remarkable activity of compound 6 against B16 melanoma tumors. A summary of the results that compares compound 6 of the present invention with selected known anti-cancer agents against B16 melanoma tumors is provided in Table 3.

TABLE 3

Evaluation of Compound 6, 22, 23, DMP840, & CYTOXAN vs. B16 Tumor In Vivo

| Compound | Dose (mg/kg) | Schedule | Route | Wt. Ch. (%) (Day 7) | T/C | 60-Day Survivors |
|---|---|---|---|---|---|---|
| 6 | 30 | q.d. × 5 | i.p. | −16.4 | 233 | 0 |
|   | 15 | q.d. × 5 | i.p. | −7.4 | 210 | 0 |
| 22 | 2.5 | q.d. × 5 | i.p. | −0.17 | 141 | 0 |
| 23 | 2.5 | q.d. × 5 | i.p. | 0.95 | 162 | 0 |
| DMP840 | 10 | q.d. × 5 | i.p. | −0.33 | 179 | 0 |
|   | 5 | q.d. × 5 | i.p. | +4.6 | 156 | 0 |
| Cytoxan | 300 | q.d. × 1 | i.p. | −6.6 | 197 | 0 |
|   | 150 | q.d. × 5 | i.p. | −12.2 | 175 | 0 |

Compound 6 had a T/C of 210 at dose level of 15 mg/kg. The highest effective dose of cytoxan was 300 mg/kg. The doses administered correspond to the maximum tolerated dose. Therefore, all of the pharmaceutical compounds are "normalized" to the highest dose that can be safely given to mice. This should produce the optimal response based on the principle of dose response.

These data show that compound 6 is more active in this model than DMP840, compounds 22 and 23, and cytoxan, a commercially sold anti-cancer drug that is useful in the treatment of cancer patients.

Other Cancers:

It is apparent from the present disclosure that the compounds of the present invention are expected to be useful in the treatment of other types of cancer, such as leukemia, breast cancer, colon cancer, and the like. The following examples are provided to illustrate some proposed in vivo studies that would support their use in treating these cancers.

P388 Leukemia:

This test can be conducted in a similar manner to the B16 test. The tumor inoculum can be prepared by removing ascites fluid containing P388 cells from tumored B6D2F1 mice, centrifuging the cells, and then resuspending the leukemia cells in saline. Mice can then receive $1 \times 10^6$ P388 cells i.p. on day 0.

MX-1 Human Breast Tumor Xenograft:

Nude mice can be implanted subcutaneously by trocar with fragments of MX-1 mammary carcinomas harvested from s.c. growing MX-1 tumors in nude mice hosts. When tumors are approximately 5 mm×5 mm in size (usually about ten days after inoculation), the animals can be pair-matched into treatment and control groups. Each group could contain 10 rumored mice, each of which was ear-tagged and followed individually throughout the experiment. The administration of drugs or vehicle can begin the day the animals are pair-matched (day 1). The doses, route of drug administration and schedule can be selected as appropriate for the study in question. If the MTD dose of an agent is not known, it can be determined in an initial dosing experiment in non-rumored mice. In a typical study, drugs can be given at their MTD and ½ MTD doses i.p. on a daily×5 schedule.

The study can usually be terminated when control tumors reach a size of 2–3 g. Mice could be weighed twice weekly, and tumor measurements taken by calipers twice weekly, starting on day one. These tumor measurements can be converted to mg tumor weight and from these calculated tumor weights, the termination date can be determined. Upon termination, all mice can be weighed, sacrificed, and their tumors excised. Tumors can be weighed, and the mean tumor weight per group calculated. In this model, the mean treated tumor weight/mean control tumor weight×100% (T/C) can be subtracted from 100% to give the tumor growth inhibition (TGI) for each group.

Some drugs may cause tumor shrinkage in the MX-1 model. With these agents, the final weight of a given tumor can be subtracted from its own weight at the start of treatment on day 1. This difference divided by the initial tumor weight can be the % shrinkage. A mean % tumor shrinkage can be calculated from data from the mice in a group that experienced MX-1 regressions. If the tumor completely disappears in a mouse, this can be considered a complete regression or complete tumor shrinkage. If desired, mice with partial or total tumor regressions can be kept alive past the termination date to see whether they live to become long term, tumor-free survivors. Statistics can be performed on the data using primarily the log rank p-value test.

EXAMPLE 5

Bis-Naphthalimides Having Two Oxygen Atoms in the Linker

Synthesis of 5-[2-(3-Nitronaphthalene-1,8-dicarboximido)ethoxy]-1-(3-nitronaphthalene-1,8-dicarboximido)-3-oxapentane (19)

Most of the compounds synthesized had at least one nitrogen in the linker. However, a compound lacking nitrogen atoms in its linker was synthesized. This compound quite unexpectedly did not bind to DNA. The bis-naphthalimide, compound 19, having two oxygen atoms was synthesized in a manner analogous to the other bis-naphthalimides of the present invention from compound 18 that was synthesized according to the literature (Gatto et al., 1986). The DNA binding ability of this compound and the in vitro growth inhibitory activity against B16 melanomas were also determined in a manner analogous to the other compounds of this invention. The binding affinity $FI_{50}$ values (μM) as measured by an ethidium bromide displacement assay for this compound are 56 for lambda DNA, 49 for poly(dG·dC)–poly(dG·dC), and 83 for poly(dA·dT)–poly(dA·dT), giving a ratio of AT/GC of 1.7. These data suggest that this compound does not interact with and bind to DNA effectively, particularly as compared to the other bis-naphthalimides of the present invention and the known anticancer agents. The in vitro tumor $IC_{50}$ value against B16 melanoma was 0.051 μM. While this compound did not bind to DNA, it nevertheless exhibited potent anticancer activity against this melanoma type. It is expected that this compound will also exhibit in vitro and in vivo anticancer activity against other melanomas, sarcomas and carcinomas.

1,2-Bis(2-azidoethoxy)ethane (17)

A mixture of 1,2-bis(2-chloroethoxy)ethane (16) (4.68 g, 25 mmol), sodium azide (6.50 g, 100 mmol), and Adogen 464 (800 mg) in water (20 mL) was heated at 98° C. for 16 hours. The reaction mixture was cooled to room temperature, and the two layers were separated. The organic layer was washed with water, brine and dried over $Na_2SO_4$ to give the crude diazide (17) (3.60 g, 72% yield). This crude diazide (17) was directly taken into the next step without further purification. IR (Neat, $cm^{-1}$) 2928, 2098, 1443, 1302, 1124.

$^1$H NMR in $CDCl_3$ (units δ): 3.38 (t, J=5 Hz, 4H), 3.67 (m, 8H).

1,8-Diamino-3,6-dioxaoctane (18)

The diazide (17) (3.55 g, 17.85 mmol) in THF (10mL) was added dropwise into a cold (−5° C.) stirred mixture of lithium aluminum hydride (1.83 g, 48.2 mmol) in THF (20 mL). The reaction mixture was kept at −5° C. and carefully quenched with water (10 mL). The THF layer was filtered to remove the inorganic salts, dried over $Na_2SO_4$, and evaporated in vacuo to afford the diamine (18) (2.56 g, 97% yield).

$^1$H NMR in $CDCl_3$ (units δ): 2.82 (t, J=5 Hz, 4H), 3.48 (t, J=5 Hz, 4H), 3.61 (s, 4H).

5-[2-(3-Nitronaphthalene-1,8-dicarboximido)ethoxy]-1,3-nitronaphthalene-1,8-dicarboximido)-3-oxapentane (19).

An ethanolic solution (25 mL) of the diamine (18) (148 mg, 1 mmol), 3-nitro 1,8-naphthalic anhydride (4) (486 mg, 2 mmol) was refluxed for 12 hours. The reaction mixture was cooled to room temperature. The precipitate was isolated by filtration and washed with ethanol and chloroform. Finally the solid was dried in vacuo to obtain the bis-naphthalimide (19) (448 mg, 75% yield). $Rf$=0.76 (5% $MeOH$-$CH_2Cl_2$), mp 213°–216° C.

$^1$H NMR in TFA-d (units δ): 3.97 (s, 4H), 4.05 (t, J=5 Hz, 4H), 4.53 (t, J=5 Hz, 4H), 7.95 (m, 2H), 8.49 (d, J=8 Hz, 2H), 8.80 (m, 2H), 9.21 (d, J=2.1 Hz, 2H), 9.33 (d, J=2.1 Hz, 2H).

EXAMPLE 6

NAPHTHALIMIDE-POLYAMINE-PLATINUM COMPLEX

8-[(3'-nitro-1',8'-naphthalimide)-3,6-diaza]octylamine trihydrochloride (also known as "N-2(-Aminoethyl)-N'-[2-(3'-nitro-1',8'-naphthalimido)ethyl]ethylene-diamine trihydrochloride") (20)

A solution of 4.0 g (7.3 mmol) of N-(2-aminoethyl)-N'-[2-(3'-nitro-1',8'-naphthalimido)ethy]ethylenediamine triacetic acid (3) in 50 mL of methanol was cooled to 0° C. While the solution was stirred, 4.0 mL (40 mmol) of con. hydrochloric acid was added drop by drop (about 15 minutes). A light yellow precipitate was formed immediately. The reaction mixture was stirred for 30 min after removing the ice-bath. The solid was filtered at suction, washed with methanol (2×25 mL), followed by ether (2×25 mL) and dried in vacuum desiccator to give 3.0 g (86%) of solid: mp 190°–193° C. (decomposes).

$^1$H-NMR ($D_2O$): δ3.46 (m, 10H), 4.50 (t, 2H), 7.93 (t, 1H), 8.48 (d, 1H), 8.64 (d, 1H), 9.00 (d, 1H), 9.19 (d, 1H).

IR (KBr): 3588, 3027, 1716, 1655, 1541 $cm^{-1}$ 8-(3'-nitro-1',8'-naphthalimide)-3,6-diazaoctylamine dichloroplatinum(II) (21)

To a solution of 96 mg (0.2 mmol) of 8-[(3'-nitro-1',8'-naphthalimide)-3,6-diaza]octylamine trihydrochloride (4) in 4.0 mL of deionized water 0.35 mL of 2N sodium carbonate was added followed by 84 mg (0.2 mmol) of $K_2PtCl_4$ in 2.0 mL of distilled water. The reaction mixture was stirred at room temperature for 24 h with aluminum foil wrapped around the flask to protect from light. After this period, 20 mL of 5% KCl was added, stirred for 2 h, filtered, washed with DI water (3×10 mL) and finally dried in vacuum oven to yield 49 mg (38%) of light purple solid: mp>260° C. (decomposes).

$^1$H-NMR (DMSO-$d_6$): δ2.6–2.9 (m, 6H), 4.0–4.6 (m, 4H), 5.4–5.7 (m, 2H), 8.07 (t, 1H), 8.67 (d, 1H), 8.79 (d, 1H), 8.95 (d, 1H), 9.50 (d, 1H).

IR (KBr): 3617, 3446, 3180, 2345, 1704, 1666, 1597, 1538, $cm^{-1}$

EXAMPLE 7

Interaction of Compound 21 with DNA

Compound 21 was designed to possess two possible modes of interaction with DNA: non-covalent (intercalation with groove binding) and covalent modification of DNA. Unexpectedly, this combination of various binding modes resulted in a potent distortion of DNA conformation. Such distortion (DNA unwinding) is seen after short times of incubation of DNA with the drug in the absence of covalent adducts. Cisplatin does not show such an effect and causes unwinding only after prolonged incubation.

The model used in this study, negatively supercoiled, closed circular, plasmid SV40 DNA (Form I), undergoes several stages of drug-induced unwinding that are monitored by agarose electrophoresis. Compound 21 gradually converts the negatively supercoiled SV40 DNA (Form I) to relaxed Form I, which comigrates with Form II (nicked) and next to positively supercoiled DNA.

Central to the understanding of compound 21 action was the ability to assess whether the drug was bound irreversibly (presumably covalently) or reversibly. The system used to extract the reversibly bound drug went through several phases of development. The classic phenol/chloroform mixture cannot completely extract all of the drug. However, the phenol/chloroform mixture effectively extracts the drug in the presence of at least 0.1M NaCl.

Three different systems, A, B and D were used to probe the mode of interaction of compound 21 with DNA.

System A: Compound 21 and DNA in TE buffer (10 mM Tris-HCl, pH 7.5 and 1 mM EDTA) without phenol/chloroform.

System B: Compound 21 and DNA in TE buffer with 0.5M NaCl without phenol/chloroform extraction.

System D: Compound 21 and DNA in TE buffer with 0.5M NaCl followed by phenol/chloroform extraction.

In general, SV40 DNA (90% Form I, negatively supercoiled, and 10% Form II, nicked, Gibco BRL) was incubated with graded concentrations of compound 21 at 37° C. for the indicated time periods in the appropriate system. The isolated DNA was then separated by agarose gel electrophoresis (1% Seakem agarose in 1× TAE buffer) in TAE buffer with 80 volts for 2 hours. Gels were stained with ethidium bromide (0.5 µg/ml) for 15 minutes, washed and then recorded with polaroid film while being irradiated with a UV transilluminator ($\lambda$=254 nm).

Results

The contribution of non-covalent and covalent interactions of compound 21 over time was deciphered with this extraction scheme. Several studies have shown that compound 21's effect on SV40 conformation is observed instantly (FIG. 3A), but without incubation, the effect of compound 21 on DNA can be completely reversed using System D (FIG. 3B). The data suggest compound 21 does not produce any apparent DNA adducts without some incubation time.

On the other hand, if DNA is incubated with compound 21 for several hours, more of the mobility shift is retained, with an actual increase in drug effect at the full 8 hours (FIG. 3C). This effect is important for in vivo applications of the invention. Since the in vivo half life of compound 21 is expected to be at least 8 to 24 hours, the covalent adducts of the drug and the DNA would be expected to be formed in the target cells in vivo. Effectively, the concentration at which form I and II comigrate decreases 2 fold from time zero to 8 hours (i.e. the summation of the two moieties' effect on unwinding the DNA is evident by the decrease in the concentration required to achieve the same degree of relaxation, or unwinding, from zero to 8 hours). Interestingly, no change in DNA mobility shift is observed even under system D at 8 hours (FIG. 3D). Since System D should remove all of the non-covalently bound compound 21, the data suggest that compound 21 forms covalent adducts with DNA after prolonged incubation. The time course studies indicate that the irreversible effect on DNA conformation reaches a plateau at 6–8 hours. Complementary to this, the same compound 21 treated DNA can be returned to normal mobility after treatment with thiourea, a nucleophile that is known to readily displace cisplatin adducts from DNA.

EXAMPLE 8

Induction of DNA Crosslinks by Compound 21

Isolated SV40 DNA (Gibco BRL) was digested with EcoRI (3 units/µg DNA) (Promega #R6011) at 37° C. for two hours, and concentrated through a spin column (Microcon 50, Amicon, Inc.). The EcoRI digested SV40 DNA was then digested with Taq I (3 units/µg DNA) (Promega #6151) at 65° C. for an additional 2 hours. After digestion, DNA was extracted once with phenol/chloroform/isoamyl alcohol (25:24:1), and once with chloroform/isoamyl alcohol (24:1). The digested DNA was then labelled on the 5' end with $^{32}$P using the DuPont/NEN T4 polynucleotide kinase 5' end labelling system and $\alpha$-$^{32}$P-ATP. Labelled DNA was loaded onto a pre-equilibrated Sephadex 25 spin purification column (Quick-spin, Boehringer-Mannheim Biochemicals) and eluted into 400 µl TE (20 mM Tris HCl, 1 mM EDTA). Eluted DNA was ethanol precipitated overnight at −20° C. and spun in an Eppendorf microcentrifuge for 1 hour at 4° C., 14,000 rpm.

Precipitated DNA was suspended in TE (20 mM Tris HCl, pH 8, 1 mM EDTA) at approximately 0.1 µg/µl and incubated at 37° C. for 17 hours in a 50 µl volume with 0, 0.5, 1.0, 1.5 or 2 µM compound 21. Following drug treatment, DNA was again ethanol precipitated, spun down, dried briefly and suspended in 20 µl water. Four microliters of loading buffer was added (0.3M sodium hydroxide, 6 mM EDTA, 18% Ficoll, 0.15% bromocresol green) and the samples were loaded on 1% alkaline agarose gels (1% Seakem agarose, 50 mM sodium hydroxide, 1 mM EDTA). The DNA fragments were separated by gel electrophoresis for 1823 volt-hours (40.5 hours at 45 volts) in 30 mM sodium hydroxide, 1 mM EDTA buffer.

Following electrophoresis, gels were neutralized by washing twice for 25 minutes each in 1M Tris-HCl (pH 8.0), 1.5M NaCl. Gels were then stained with ethidium bromide and photographed using a polaroid filter and 254 nm UV transilluminator. Ethidium bromide was removed by washing twice for 15 minutes each in 1× tris-acetate-EDTA electrophoresis buffer. Destained gels were dried onto Whatman 3 MM paper at 45° C. for three hours and exposed to Kodak X-AR film for 2 hours with an intensifying screen.

Results

Figure 4:
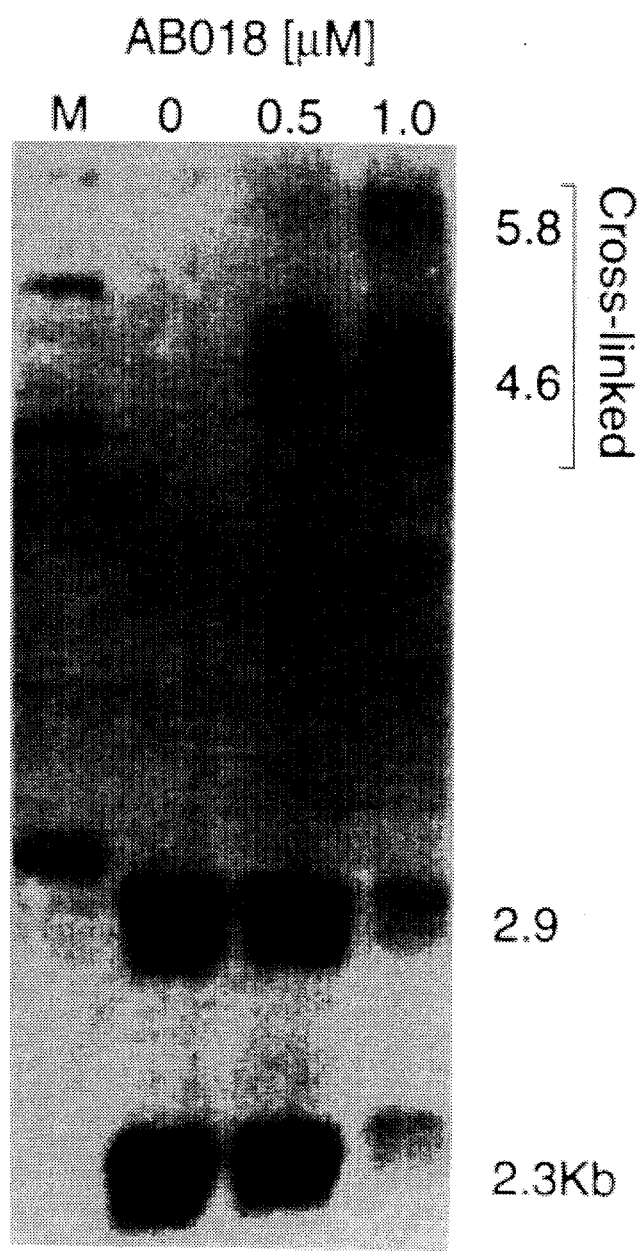
FIG. 4. Agarose gel demonstrates cross-linked DNA of 4.6–5.8 Kb in the presence of 0.5 and 1 μM compound 21.

The results are shown in FIG. 4. Two linear DNA fragments of 2286 and 2957 base pairs, respectively, were produced from EcoRI and Taq1 digested SV40 DNA. The 5' end labelled DNA fragments of the control lane (no compound 21 added) shows two bands at 2.3 and 2.9 Kb, corresponding to the 2286 and 2957 bp DNA from SV40. The formation of higher molecular weight DNA, around 4.6 and 5.8 Kb, in the presence of 0.5 and 1 µM compound 21 suggests the formation of DNA cross links by compound 21.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,874,863
U.S. Pat. No. 5,086,059
U.S. Pat. No. 5,206,249
U.S. Pat. No. 5,206,250
U.S. Pat. No. 5,235,045
Arthaud et al. (1993) *Proc. Am. Ass. Cancer Res.*, 34:384, Abstract #2290.
Bosquet et al. (1993) *Proc. Am. Ass. Cancer Res.*, 34:374, Abstract #2230.
Brana et al. (1993) *Proc. Am. Ass. Cancer Res.*, 34:383, Abstract #2285.
Calabresi and Chabner (1990) In: Gilman et al. eds. *The Pharmacological Basis of Therapeutics*, 8th ed. Pergamon Press:New York, pp. 1209–1263.
Chen et al. (1993) *Anti-Cancer Drugs*, 4:447.
Chen et al. (1993) *Proc. Am. Ass. Cancer Res.*, 34:348, Abstract #2074.
Cornbleet et al. (1984) *Eur. J. Cancer Clin. Oncol.*, 20:1141.
Czerniak et al. (1993) *Proc. Am. Ass. Cancer Res.*, 34:384, Abstract 190 2289.
Denny (1983) In:Neidle and Waring eds. *Molecular Aspects of Anti-Cancer Drug Action*, MacMillan:London, pp. 1–34.
Gatto et al. (1986) *J. Org. Chem.* 51:5373–5384.
Goldin et al. (1981) *Eur. J. Cancer* 17:129–142.
Hsiang et al. (1989) *Mol. Pharm.* 36:371–376.
Hodgson et al. (1945) *J. Chem. Soc.*, p90.
McRipley et al. (1993) *Proc. Am. Ass. Cancer Res.*, 34:384, Abstract #2291.
Papp et al. (1993) *Proc. Am. Ass. Cancer Res.*, 34:384, Abstract #2288.
Qian et al. (1993) *Proc. Am. Ass. Cancer Res.*, 34:426, Abstract #2542.
Stafford et al. (1993) *Proc. Am. Ass. Cancer Res.*, 34:384, Abstract #2292.
Sun et al. (1993) *Proc. Am. Ass. Cancer Res.*, 34:384, Abstract #2287.
Talbot et al. (1991) *J. Clin. Oncol.*, 9:2141.

What is claimed is:

1. A compound, or a pharmaceutically acceptable salt thereof, the following formula:

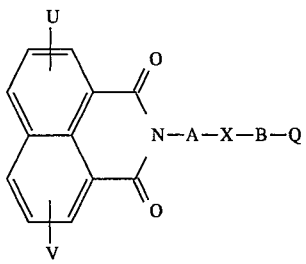

wherein X is CH, O, S, SO, $SO_2$, or $NR_1R_2$; wherein $R_1$ and $R_2$ are separately and independently hydrogen, or alkyl of from one to five carbons; wherein A and B are independently alkyl having a straight chain component of 2–4 carbon atoms where each carbon atom is bonded to H or an alkyl having up to 2 carbon atoms; wherein U and V are separately and independently hydrogen, nitro, amine, hydroxyl, alkoxy, halogen, trihalomethyl, alkyl, aryl, formyl, alkylcarbonyl, ureyl, alkylureyl or alkylcarbonylamino; and wherein Q is a diamine complexed with platinum.

2. The compound of claim 1, wherein A and B are each ethylene, X is NH and Q is ($-NH-CH_2CH_2-NH_2$)Pt(II)$Cl_2$.

* * * * *